United States Patent
Maliga

(10) Patent No.: US 9,434,952 B2
(45) Date of Patent: Sep. 6, 2016

(54) SELECTABLE MARKER GENE AND METHODS OF USE THEREOF IN TRANSPLASTOMIC PLANTS

(75) Inventor: Pal Maliga, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 571 days.

(21) Appl. No.: 13/326,295

(22) Filed: Dec. 14, 2011

(65) Prior Publication Data

US 2012/0151627 A1 Jun. 14, 2012

Related U.S. Application Data

(60) Provisional application No. 61/422,952, filed on Dec. 14, 2010.

(51) Int. Cl.
*C12N 15/82* (2006.01)

(52) U.S. Cl.
CPC ....... *C12N 15/8214* (2013.01); *C12N 15/8212* (2013.01)

(58) Field of Classification Search
CPC .................................................. C12N 15/8214
See application file for complete search history.

(56) References Cited

U.S. PATENT DOCUMENTS 5,877,402 A * 3/1999 Maliga et al. ................. 800/298
6,987,215 B1 * 1/2006 Maliga et al. ................. 800/298

OTHER PUBLICATIONS

Kittiwingwattana et al (2007, Plant Mol. Biol. 64:137-143).*
Lutz et al (2008, Plant J. 56:975-983).*
Kuroda et al (2002, Plant Physiol. 129:1600-1606).*
Tungsuchat-Huang et al, 2011, GenBank accession No. HQ023426.*
Tungsuchat-Huang et al (2011, Plant Mol. Biol. 76:453-461; published online Dec. 31, 2010).*
Allison et al., Deletion of rpoB reveals a second distinct transcription system in plastids of higher plants, EMBO J., 1996, 2802-2809,15.
Apel et al., Enhancement of carotenoid biosynthesis in transplastomic tomatoes by induced lycopene-to-provitamin A conversion, Plant Physiol., 2009, 59-66, 151.
Baena-Gonzales et al., Deletion of the tobacco plastid psbA gene triggers post-transcriptional up-regulation of thylakoid-associated terminal oxidase (PTOX) and the NAD(P)H complex, Plant J., 2003, 704-716, 35.
Barone et al., Tobacco plastid transformation using the feedback• insensitive anthranilate synthase [alpha]-subunit of tobacco (ASA2) as a new selectable marker, J Exp Bot., 2009, 3195-3202, 60.
Bock et al., Plastid biotechnology: prospects for herbicide and insect resistance, metabolic engineering and molecular fanning, Cum Opin. Biotechnol., 2007, 100-106, 18.
Carrer et al., Kanamycin resistance as a selectable marker for plastid transformation in tobacco, Mol Gen Genet., 1993, 49-56, 241.
Church et al., Genomic sequencing, Proc Natl Acad Sci USA, 1994, 1991-1995, 81.
Daniell et al., Chloroplast-derived vaccine antigens and other therapeutic proteins, Vaccine, 2005, 1779-1783, 23.
Huang et al., Efficient plastid transformation in tobacco using the aphA-6 gene and kanamycin selection, Mol Genet Genomics, 2002, 19-27, 268.
Kanevski et al., Relocation of the plastid rbcL gene to the nucleus yields functional ribulose-1,5-bisphosphate carboxylase in tobacco chloroplasts, Proc Natl Acad Sci USA, 1994, 1969-1973, 91.
Kittiwongwattana et al., Plastid marker gene excision by the phiC31 phage site-specific recombinase. Plant Mol Biol, 2007, 137-143, 64.
Kuroda et al., Complementarity of the 16S rRNA penultimate stem with sequences downstream of the AUG destabilizes the plastid mRNAs, Nucleic Acids Res., 2001a, 970-975, 29.
Kuroda et al., Sequences downstream of the translation initiation codon are important determinants of translation efficiency in chloroplasts. Plant Physiol., 2001b, 430-436, 125.
Kuroda et al., Over-expression of the clpP 51-UTR in a chimeric context causes a mutant phenotype suggesting competition for a c/pP-specific RNA maturation factor in tobacco chloroplasts, Plant Physiol., 2002, 1600-1606, 129.
Lutz et al., A novel approach to plastid transformation utilizes the phiC31 phage integrase, Plant J., 2004, 906-913, 37.
Lutz et al., A guide to choosing vectors for transformation of the plastid genome of higher plants. Plant Physiol., 2007, 1201-1210, 145.
Lutz et al., Expression of bar in the plastid genome confers herbicide resistance, Plant Physiol., 2007, 1585-1590, 125.
Lutz et al., Transformation of the plastid genome to study RNA editing, Methods Enzymol., 2007, 501-518, 424.
Lutz et al., Plastid genomes in a regenerating tobacco shoot derive from a small number of copies selected through a stochastic process, Plant J., 2008, 975-983, 56.
Lutz et al., Construction of marker-free transplastomic tobacco using the Cre-loxP site-specific recombination system, Nat Protocols, 2006, 900-910, 1.
Madoka et al., Chloroplast transformation with modified accD operon increases acetyl-Co-A carboxylaase and causes extension of leaf longevity and increase in seed yield in tobacco, Plant and Cell Physiology, 2002, 1518-1525, 43.
Maliga et al., Plastid transformation in higher plants, Ann Rev Plant Biol, 2004, 289-313, 55.
Murashige et al., A revised medium for the growth and bioassay with tobacco tissue culture, Physiol Plant, 1962, 473-497, 15.
Murray et al., Rapid isolation of high molecular weight plant DNA. Nucleic Acids Res., 1980, 4321-4325, 8.
Sharwood et al., The catalytic properties of hybrid rubisco comprising tobacco small and sunflower large subunits mirror the kinetically equivalent source Rubiscos and can support tobacco growth, Plant Physiol., 2008, 83-96, 146.
Sinagawa-Garcia et al., Next generation synthetic vectors for transformation of the plastid genome of higher plants, Plant Mol Biol., 2009, 487-498, 70.

(Continued)

Primary Examiner — Anne Kubelik
(74) Attorney, Agent, or Firm — Kathleen D. Rigaut; Dann, Dorfman, Herrell & Skillman

(57) ABSTRACT

Compositions and method for the generation of transplastomic plants are provided.

11 Claims, 12 Drawing Sheets

(56) References Cited

OTHER PUBLICATIONS

Sprengart et al., The downstream box: an efficient and independent translation initiation signal in *Escherichia coli*, EMBO J.,2006, 665-674, 15.
Sriraman et al., The phage-type PclpP-53 plastid promoter comprises sequences downstream of the transcription initiation site, Nucleic Acids Res., 1998, 4874-4879, 26.
Suzuki et al., Unique architecture of the plastid ribosomal RNA operon promoter recognized by the multisubunit Rna polymerase (PEP) in tobacco and other higher plants, Plant Cell, 2003, 195-205, 15.
Svab et al., High-frequency plastid transformation in tobacco by selection for a chimeric aadA gene, Proc Natl Acad Sci USA, 1193, 913-917, 90.
Tungsuchat-Huang et al., Study of plastid genome stability in tobacco reveals that the loss of marker genes is more likely by gene conversion than by recombination between 34-bp IoxP repeats, Plant Physiol., 2010, 252-259, 153.
Wakasugi et al., The genomics of land plant chloroplasts: gene content and alteration of genomic information by RNA editing, Photosynth Res, 2001, 107-118, 70.
Whitney et al., Plastome-encoded bacterial ribulose-1,5-bisphosphate carboxylase/oxygenase (Rubisco) supports photosynthesis and growth of tobacco, Proc Natl Acad Sci USA, 2001, 14738-14743, 98.
Whitney et al., Photosynthesis and growth of tobacco with substituted bacterial rubisco mirror the properties of the introduced enzyme, Plant Physiol., 2003, 287-294, 133.
Ye et al., Persistance of unselected transgenic DNA during a plastid transformation and segregation approach to herbicide resistance, Plant Physiol., 2003, 402-410, 133.
Day et al., The chloroplast transformation toolbox: selectable markers and marker removal, Plant Biotechnology Journal, 2011, 540-553, 9.
Ruf et al., Stable genetic transformation of tomato plastids and expression of a foreign protein in fruit, Nature, 2001, 870-875, 19.
Ruhlman et al., The Role of Heterologous Chloroplast Sequence Elements in Transgene Integration and Expression, Plant Physiol., 2010, 2088-2104, 152.
Singh et al., Plastid transformation in eggplant (Solanum melongena L.), Transgenic Research, 2010, 113-119, 19.
Tungsuchat-Huang et al., Visual spectinomycin resistance (aadAau) gene for facile identification of transplastomic sectors in tobacco leaves, Plant Mol Biol., 2011, 453-461, 76.
Wei et al., Transformation of alfalfa chloroplasts and expression of green fluorescent protein in a forage crop, Biotechnol Lett, 2011, 2487-2494, 2487-2494, 33.

* cited by examiner

| Plasmid | Chimeric genes | Aurea phenotype | No. genes per ptDNA |
|---|---|---|---|
| pSS42 | Prrn::PclpP::LrbcL — bar — TrbcL | ++++ | 2 |
| pSS52 | Prrn::PclpP::LrbcL — aadA — c-myc TpsbA | + | 2 |
| pKMS10 | Prrn::PclpP::LclpP — aadA — c-myc TpsbA | ++ | 2 |
| pKMS8 | Prrn::PclpP::LclpP+DB — aadA — c-myc TpsbA | ++++ | 2 |
| pKMS12 | Prrn::PclpP::LclpP+DB — aadA — c-myc TpsbA | +++ | 1 |

(B)

PrrnPclpPrbcL (pCK2, pSS42 and pSS52)

```
     SacI
  1  gagctcGCTC CCCCGCCGTC GTTCAATGAG AATGGATAAG AGGCTCGTGG
 51  GATTGACGTG AGGGGGCAGG GATGGCTATA TTTCTGGGAG TTACGTTTCC
                                          BsaAI  BsaI
101  ACCTCAAAGT GAAATATAGT ATagttgtag ggagggatccATGG
```

PrrnPclpP+DB (pHK32, pKMS8 and pKMS12)

```
     SacI
  1  gagctcGCTC CCCCGCCGTC GTTCAATGAG AATGGATAAG AGGCTCGTGG
 51  GATTGACGTG AGGGGGCAGG GATGGCTATA TTTCTGGGAG TTACGTTTCC
101  ACCTCAAAGT GAAATATAGT ATTAGTTCT TTCTTTCATT TAATGCCTAT
151  TGGTGTTCCA AAAGTCCCTT TCCGAAGTCC TGGAGGGAA gctagc
                                                 XbaI
```

PrrnPclpP (pHK33 and pKMS10)

```
     SacI
  1  gagctcGCTC CCCCGCCGTC GTTCAATGAG AATGGATAAG AGGCTCGTGG
 51  GATTGACGTG AGGGGGCAGG GATGGCTATA TTTCTGGGAG TTACGTTTCC
                                                      XbaI
101  ACCTCAAAGT GAAATATAGT ATTAGTTCT TTCTTTCATT TAATGCCTgc
151  tagc
```

Figure 4
(A) wt-ptDNA
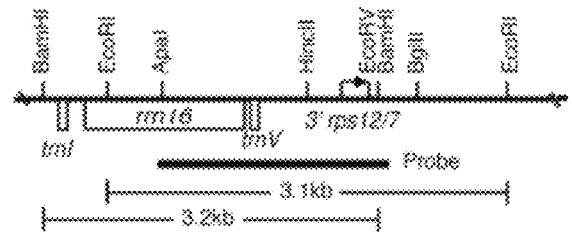
Nt-pKMS8
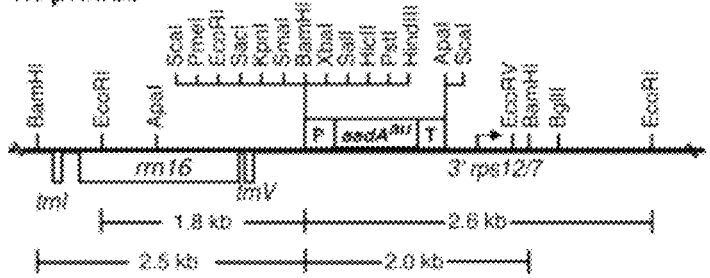
(B) EcoRI digested pt-DNA (1X regerated)
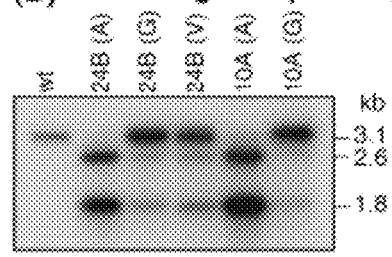
BamHI digested pt-DNA (2X regenerated)
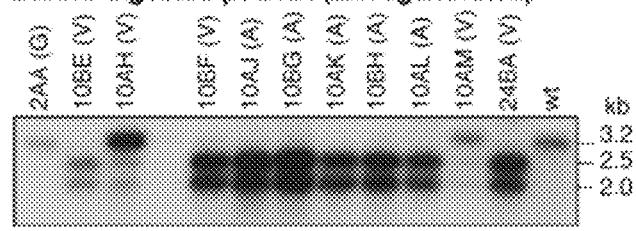

Figure 9
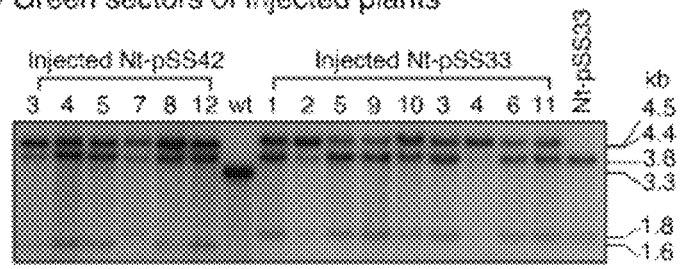
(a) Green sectors of injected plants
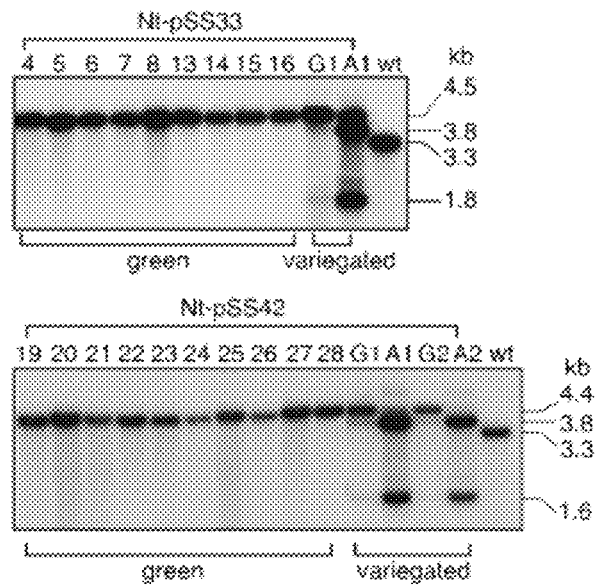
(b) Seed progeny of injected plants

SELECTABLE MARKER GENE AND METHODS OF USE THEREOF IN TRANSPLASTOMIC PLANTS

This Application claims priority to U.S. Provisional Application No. 61/422,952 filed Dec. 14, 2010, the entire disclosure being incorporated herein by reference as though set forth in full.

Pursuant to 35 U.S.C. §202(c) it is acknowledged that the U.S. Government has rights in the invention described, which was made in part with funds from the USDA National Institute of Food and Agriculture Biotechnology Risk Assessment Research Grant Program, Grant Numbers 2005-33120-16524 and 2008-03012.

FIELD OF THE INVENTION

This invention relates to the fields of molecular biology and transplastomic plants. More specifically the invention provides a selectable marker encoding nucleic acid and methods of use thereof for the production of transgenic plants having desirable characteristics.

BACKGROUND OF THE INVENTION

Several publications and patent documents are cited throughout the specification in order to describe the state of the art to which this invention pertains. Each of these citationsis incorporated herein by reference as though set forth in full.

Angiosperm plastids carry a relatively small genome (ptDNA), which is 120 kb to 160 kb in size and encodes ~130 genes (Raubeson and Jansen 2005). These genes include some, but not all genes required for plastid transcription and translation. In addition, plastid genes encode photosystem, ATPase and NDH subunits, a gene involved in protein degradation and another in lipid biosynthesis (Wakasugi, et al. 2001). Transformation of the plastid genome is employed to probe plastid gene function in knockout plants and to beneficially alter processes localized to plastids, for example photosynthesis (Sharwood, et al. 2008, Whitney and Andrews 2001, Whitney and Andrews 2003), lipid biosynthesis (Madoka, et al. 2002) and the biosynthesis of vitamins (Apel and Bock 2009). Transformation is also used to incorporate novel genes in the ptDNA for the production of industrial enzymes and pharmaceutical proteins. For reviews see (Bock 2007, Daniell, et al. 2005, Maliga 2004).

Plastid transformation is based on homologous recombination between the ptDNA and ptDNA fragments in the vectors flanking a marker gene. Because plant cells contain hundreds to thousands of ptDNA copies, selective amplification of the transformed ptDNA copy is important for the recovery of transplastomic clones. According to the commonly used protocol, the tobacco leaves are bombarded with DNA-coated gold particles, then the leaves are cut into small pieces and transferred to a shoot regeneration medium containing spectinomycin. The selective medium suppresses greening and shoot regeneration of wild type cells and the transplastomic clones are identified as green shoots. The shoots regenerating from the bombarded leaves are chimeric. Genetically stable plants with a uniform population of transformed ptDNA (homoplastomic plants) are obtained by regenerating new shoots from the chimeric leaves. Typically two cycles of such purifying regeneration are required to obtain homoplastomic plants. Marker genes available in plastids for selective enrichment confer resistance to spectinomycin and streptomycin (aadA) (Svab and Maliga 1993), kanamycin (neo or aph(3')IIa) (Caner, et al. 1993, Huang, et al. 2002) (Lutz, et al. 2004), chloramphenicol (Li, et al. 2011) or the amino acid analogues 4-methylindole (4MI) and 7-methyl-DL-tryptophan (7MT) (ASA2) (Barone, et al. 2009). Because the plants that are expressing marker genes have no visual phenotype, homoplastomic state can be verified only by DNA gel blot analyses.

It is clear that selectable marker genes conferring a visibly detectable phenotype are highly desirable. It is an object of the invention to provide such marker genes.

SUMMARY OF THE INVENTION

In accordance with the present invention an isolated nucleic acid encoding a visibly detectable selectable marker for identification of transformed plastids wherein said nucleic acid encodes aadA$^{au}$ is provided. In another embodiment, the nucleic acid is contained within a vector suitable to transform higher plants. In yet another aspect, the vector may comprise a heterologous nucleic acid encoding a protein of interest. Plant cells transformed with the nucleic acid or vectors described herein are also encompassed by the present invention as are plants comprising the same.

In yet another embodiment, methods for obtaining transplastomic plants are disclosed. An exemplary method entails introducing the nucleic acid encoding the visibly detectable marker gene into a plant cell and selecting those transformed cells which exhibit the golden leaf phenotype and spectinomycin resistance, regenerating shoots from said transformed cells, and rooting said shoots in soil under conditions suitable to generate said transplastomic plant. In one approach, the nucleic acid in introduced using a suitable plastid transformation vector which can optionally encode one or more heterologous proteins of interest. Plants obtained by the foregoing methods are also within the scope of the present invention.

In another aspect of the invention, a method for in planta selectable marker gene excision is disclosed. An exemplary method comprises providing a plant comprising plastids transformed with a nucleic acid encoding a selectable marker gene, the marker gene comprising a nucleic acid sequence which upon effective excision from plastids, confers a phenotype on a plant cell or plant sector that is identifiable via visual inspection, the nucleic acid being flanked by excision sites. A nucleic acid encoding a recombinase which acts on said excision sites is delivered directly to cells positioned in the plant body of a) to form a shoot apex under conditions suitable for recombinase expression, thereby effecting recombinase mediated excision of the selectable marker gene. Those sectors which lack the selectable marker gene and as a result exhibit a dark green color in cells which contribute to the germline of progeny plants and at least one bud and/or branch associated therewith are visually selected; and seed is then collected. Also within the scope of the invention are plants obtained from the method described above and seed and progeny obtained from said plant. In a preferred embodiment, the selectable marker gene is present in a vector. In a particularly preferred embodiment, the vector is pKMS8 or pKMS12 which further comprise excision sites which flank said selectable marker gene.

In another embodiment of the invention, a method for in planta plastid transformation is disclosed. An exemplary method entails providing a nucleic acid construct encoding i) a selectable marker gene operably linked to ii) a sequence which upon expression confers a phenotype on a plant cell or plant sector that is identifiable via visual inspection operably linked to iii) a nucleic acid encoding a heterologous nucleic acid encoding a protein of interest, sequence; wherein i, ii, and iiii are flanked by plastid DNA sequences which enable homologous recombination into the plastids of the plant to be transformed. In the method, the construct is delivered to cells positioned in the plant body to form a shoot apex and shoot formation is induced in said plant. Sectors which exhibit golden leaf phenotype and least one bud and/or branch associated therewith are then selected and seed collected from resulting branches. Seed so produces also provide an embodiment of the invention.

BRIEF DESCRIPTION OF THE DRAWINGS

FIG. 2 Chimeric aadA genes to induce aurea phenotype in plants. a AureaaadA$^{au}$ genes have unique 5' regulatory sequences (FIG. 2b) and share the aadA coding region (fused with c-myc tag; filled box) along with TpsbA (3'-UTR or transcription terminator). On top is the reference aurea bar$^{au}$ gene encoded in plasmid pSS42 (Tungsuchat-Huang, et al. 2010). The black box schematically depicts clpP1 sequence. The intensity of aurea phenotypes (four to one plus marks for the most to least intense) and the number of aadA$^{au}$ gene copies per ptDNA are also listed. b DNA sequence of 5'regulatory regions of aurea aadA$^{au}$ genes (SEQ ID NOs: 1-3 from top to bottom). Nucleotides comprising the rrn16 PEP promoter (Prrn) (Suzuki, et al. 2003) are in capital letter and underlined; the clpP1-53 NEP promoter (PclpP), the ClpP leader and ClpP protease subunit coding sequences are in capital letters (not underlined); the minimal clpP1-53 promoter that was defined in plasmid pPS45 (Sriraman, et al. 1998) is boxed. Within Prrn, the plastid rRNA upstream activator (RUA, GTGGGA; italics) and rrn16 promoter-35 (TTGACG; bold) and -10 (TATATT; bold) sequences are marked (Suzuki, et al. 2003). Aurea genes in plasmids pCK2 and pSS52 have the rbcL leader (nucleotides in lower case); in plasmids pKMS12 the clpP1 leader; (nucleotides in capital letters); and in pKMS8 and pKMS12 the clpP1 leader and 14 amino acids of the coding region N-terminus (PclpP+DB; nucleotides in capital letters). Plasmids, which carry transgenes with the same 5'-regulatory region are listed including: pCK2 (Kittiwongwattana, et al. 2007); pSS42 (Tungsuchat-Huang, et al. 2010); pHK32 (unpublished); and pHK33 (Kuroda and Maliga 2002).

FIG. 4 DNA gel blot analyses of Nt-pKMS8 leaves provide confirmation that the aurea sectors contain transformed plastids. a Maps of the transformed ptDNA in Nt-pKMS8 plants and the cognate region in wild type ptDNA. Map position of the plastid rrn16, trnV and 3'-rps12/7 leader and the probe are shown. b DNA gel blot analyses of variegated leaf sectors. Leaf phenotypes are given in parenthesis above the lanes. Abbreviations: A, aurea; G, green; V, variegated.

FIG. 9. DNA analyses confirm marker excision in green leaves. Total cellular DNA was digested with the BamHI restriction endonuclease and probed with the ApaI-BamHI targeting region fragment. Predicted BamHI fragment sizes are shown in FIG. 1a-c. (a) DNA gel blot analyses of green sectors in the Agroinjected plants. Note that all samples are heteroplastomic due to chimeric leaf structure or mixed plastids. (b) DNA gel blot analyses of Agroinjected Nt-pSS33 and Nt-pSS42 seed progeny. Lanes contained DNA from individual seedlings of Nt-pSS33(I3-2, lanes 4, 13-16, G1/A1; 13-5, lanes 5-8) and Nt-pSS42(I11-1, lanes 25-28; I11-11, lanes 19,20; I3-6, lanes 21-24, G1/A1, G2/A2).

DETAILED DESCRIPTION OF THE INVENTION

Figure 1:
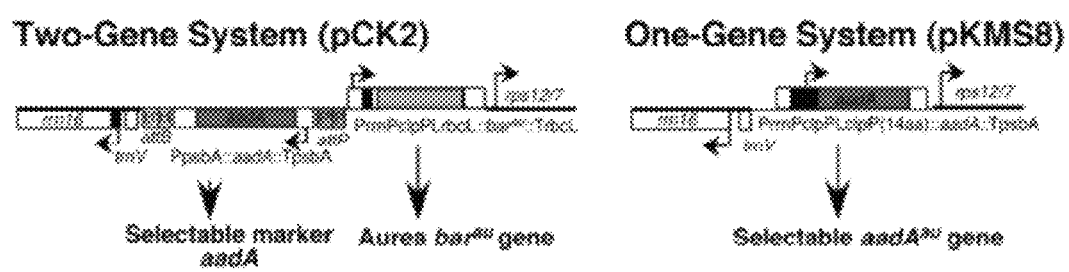
FIG. 1 The two-gene and new one-gene aurea marker systems. In the two-gene pCK2 vector bar$^{au}$ confers the aurea phenotype and aadA is the selective marker (Kittiwongwattana, et al. 2007). In the new one-gene aurea vector pKCMS8 aadA$^{au}$ performs both roles: confers the aurea phenotype and is the selective marker. Flanking ptDNA encoding the rrn16 and trnV genes (on the left) and rps12/7 (on the right) target the insertion of transgenes by homologous recombination.

Identification of a genetically stable *Nicotiana tabacum* (tobacco) plant with a uniform population of transformed plastid genomes (ptDNA) takes two cycles of plant regeneration from chimeric leaves and analysis of multiple shoots by Southern probing in each cycle. Visual detection of transgenic sectors facilitates identification of transformed shoots in the greenhouse, complementing repeated cycles of blind purification in culture. In addition, it provides a tool to monitor the maintenance of transplastomic state. Our current visual marker system requires two genes: the aurea bar (bar$^{au}$) gene that confers a golden leaf phenotype and a spectinomycin resistance (aadA) gene that is necessary for the introduction of the bar$^{au}$ gene in the plastid genome. We developed a novel aadA gene that fulfills both functions: it is a conventional selectable aadA gene in culture, and allows detection of transplastomic sectors in the greenhouse by leaf color.

Common causes of pigment deficiency in leaves are mutations in photosynthetic genes, which affect chlorophyll accumulation. We use a different approach to achieve pigment deficiency: post-transcriptional interference with the expression of the clpP1 plastid gene by aurea aadA$^{au}$ transgene. This interference produces plants with reduced growth and a distinct color, but maintains a wild-type gene set and the capacity for photosynthesis. Importantly, when the aurea gene is removed, green pigmentation and normal growth rate are restored. Because the aurea plants are viable, the new aadA$^{au}$ genes are useful to query rare events in large populations and for in planta manipulation of the plastid genome.

The following definitions are provided to aid in understanding the subject matter regarded as the invention.

"Heteroplastomic" refers to the presence of a mixed population of different plastid genomes within a single plastid or in a population of plastids contained in plant cells or tissues.

"Homoplastomic" refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

"Plastome" refers to the genome of a plastid.

"Transplastome" refers to a transformed plastid genome.

Transformation of plastids refers to the stable integration of transforming DNA into the plastid genome that is transmitted to the seed progeny of plants containing the transformed plastids.

A "selectable marker gene" refers to a gene that upon expression confers a phenotype by which successfully transformed plastids or cells or tissues carrying the transformed plastid can be identified. Selectable marker genes as used herein can confer resistance to a selection agent in tissue culture and/or confer a phenotype which is identifiable upon visual inspection. Thus, in one embodiment the selectable marker gene can act as both the selection agent and the agent which enables visual identification of cells comprising transformed plastids. In an alternative embodiment, the selectable marker encoding nucleic acid comprises two sequences, one encoding a molecule that renders cells resistant to a selection agent in tissue culture and another that enables visual identification of cells comprising transformed plastids.

Transforming DNA refers to homologous DNA, or heterologous DNA flanked by homologous DNA, which when introduced into plastids becomes part of the plastid genome by homologous recombination.

"Agroinfiltration" refers to *Agrobacterium* mediated T-DNA transfer. Specifically, this process involves vacuum treatment of leaf segments in an *Agrobacterium* suspension and a subsequent release of vacuum, which facilitates entry of bacterium cells into the inter-cellular space.

"T-DNA" refers to the transferred-region of the Ti (tumor-inducing) plasmid of *Agrobacterium* tumefaciens. Ti plasmids are natural gene transfer systems for the introduction of heterologous nucleic acids into the nucleus of higher plants:

A "plant sector" refers to a region or a full leaf of a plant that is visually identifiable due to expression of a selectable marker gene or the excision of a selectable marker gene in accordance with the present invention.

"Operably linked" refers to two different regions or two separate genes spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid; bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis.

All amino-acid residue sequences represented herein conform to the conventional left-to-right amino-terminus to carboxy-terminus orientation.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

A "clone" or "clonal cell population" is a population of cells derived from a single cell or common ancestor by mitosis.

A "cell line" is a clone of a primary cell or cell population that is capable of stable growth in vitro for many generations.

The following materials and methods are provided to facilitate the practice of the present invention.

Plastid Transformation Vectors

We describe four new plasmids in Example I, pSS52, pKMS8, pKCMS10 and pKCMS12 carrying promoter variants of aurea aadA$^{au}$ genes. DNA sequence of the promoters is shown in FIG. 2b. Plasmids pSS52, pKMS8, pKCMS10 are pPRV1-II vector derivatives targeting insertions of aadA$^{au}$ between the trnV and 3'-rps12 plastid genes localized in the repeat region of the ptDNA. Plasmid pKMS12 is a pSS22 vector (FJ416604) derivative targeting insertion of the aadA$^{au}$ in the large single copy region between the rbcL and accD genes. Plastid genomes transformed with plasmids pKMS 12 carry one copy of aadA$^{au}$, while plastids transformed with plasmids pSS52, pKMS8 and pKMS10 carry two copies of aadA$^{au}$. The promoters drive the expression of a c-myc tagged aadA coding region (SEQ ID NO: 7) and psbA 3'-UTR. DNA sequence of the aadA$^{au}$ gene is deposited in GenBank under accession number HQ023426 as part of plasmid pKMS8 DNA sequence (SEQ ID NO: 6).

Plastid Transformation

The *Nicotiana tabacum* cv. Petit Havana plastid genome was transformed using the biolistic protocol as previously described (Lutz and Maliga 2007, Lutz, et al. 2006, Svab and Maliga 1993). Briefly, 0.6 μm gold particles were coated with plasmid DNA and nine plates containing tobacco leaves were bombarded with each plasmid using the Du Pont PDA1000He biolistic gun. Transplastomic clones were selected on RMOP medium containing 500 mg l$^{-1}$ spectinomycindihydrochloride. Shoots developing on the selective medium were dissected and rooted on MS medium containing salts and 3% sucrose (Murashige and Skoog 1962).

Testing the Aurea Phenotype

Plants were transferred to soil (ProMix General Purpose Growing Medium Code 0432, Premier Horticulture Inc., Grower Services, Quakertown, Pa. 18951) in the greenhouse and fertilized weekly with a liquid solution of Blu-Grow 10-10-10 General Purpose Liquid Fertilizer (Plant Food Company, Cranbury, N.J. 08512) supplemented with monthly applications of Osmocote Classic 14-14-14 Controlled Release Fertilizer (Scotts-Sierra Horticultural Products Co., Marysville, Ohio 43401). Seeds were collected 5-6 months after the plants had been transferred to soil. Seedling phenotype in the greenhouse was scored three weeks after sowing in soil. Seedling phenotype in culture was evaluated two weeks after germinating seed on the surface of MS medium (salts plus 3% sucrose) (Murashige and Skoog 1962) in 100×20 mm Petri dishes. The seeds were vapor sterilized for 3 hours in open Eppendorf tubes in a desiccation chamber above a mix of 100 ml commercial bleach and 3 ml of concentrated hydrochloric acid.

Plastid DNA Analysis

Plastid DNA analysis has been described in previous protocols (Lutz and Maliga 2007, Lutz, et al. 2006). Briefly, total leaf cellular DNA was isolated from leaves by the CTAB protocol (Murray and Thompson 1980) and digested with appropriate restriction endonucleases. The DNA fragments were separated by electrophoresis in 0.8% agarose gels and then transferred to Hybond-N membranes (GE healthcare, UK). Hybridization was carried out in Church buffer (Church and Gilbert 1984). Double stranded DNA probes were the 2.0-kb ApaI-BamHI fragment containing the rrn16 gene and the 3.1-kb SwaI-SwaI fragment from plasmid pSS16 (Sinagawa-Garcia, et al. 2009). The probes were labeled using the Ready-To-Go DNA Labeled Beads (dCTP) (Amersham Pharmacia Biotech UK Ltd., Amersham Place, Little Chalfont Buckinghamshire, England HP7 9NA).

The following example is provided to facilitate the practice of the present invention. It is not intended to limit the invention in any way.

Example 1

Visual Spectinomycin Resistance (aadA$^{au}$) Gene for Facile Identification of Transplastomic Sectors in Tobacco Leaves Engineering the rrn16-clpP1 Dual Promoter to Induce an Aurea Phenotype The first promoter that yielded a pigment deficient aurea phenotype was serendipitously discovered in Nt-pHK33 transplastomic plants when testing translation efficiency from the plastid rRNA operon promoter (PrrnP1) fused with the 5'untranslated region (5'-UTR) of the plastid clpP1 gene (Kuroda and Maliga 2002). Because the PclpP 1-53 promoter in plasmid pHK33 initiates transcription upstream the promoter (Sriraman, et al. 1998), the kanamycin resistance (neo) gene in Nt-pHK33 plastids is expressed from two promoters: the PrrnP1 promoter initiating transcription downstream (Suzuki, et al. 2003) and the PclpP1-53 promoter initiating transcription upstream the promoter consensus. The two promoters overlap at a G nucleotide that is the transcription initiation site in both promoters (FIG. 2b). The mild aurea phenotype of Nt-pHK33 plants was attributed to reduced availability of the ClpP1 protease subunit (Kuroda and Maliga 2002). To minimize the aurea phenotype, the size of the clpP1 fragment in plasmid pCK2 (Kittiwongwattana, et al. 2007) was trimmed to the minimal PclpP1-53 promoter, as it is present in plasmid pPS45 (Sriraman, et al. 1998). The aurea phenotype, instead of being weaker, became more prominent in the Nt-pCK2 plants. The difference between the chimeric genes in plasmids pHK33 and pCK2 was not only in the promoter, but also in the coding regions: in plasmid pHK33 the chimeric promoter drives a neo gene, in plasmid pCK2 a bar gene. We decided to engineer aadA to endow it with the ability to confer visual selection. We first expressed an aadA gene in the cassette that drives the expression of bar in plasmid pCK2. We have found that the Nt-pSS52 plants had only a mild aurea phenotype as compared to the Nt-pSS42 plants (see below), which carry the aurea bar$^{au}$gene first described in the Nt-pCK2 plants (Tungsuchat-Huang, et al. 2010). We assumed that the reduced aurea phenotype this time was due to expressing aadA instead of the bar coding region. Therefore, we created three additional aadA constructs, one of which (pKMS10) has the clpP1 5'-UTR and two plasmids (pKMS8 and pKMS12) which have the clpP1 5'-UTR and 14 amino acids of the ClpP1 N-terminus that comprises the Downstream Box (DB) sequence (Kuroda and Maliga 2001a, Kuroda and Maliga 2001b, Sprengart, et al. 1996). Plasmids pKMS8 and pKMS12 target insertions in different regions in the ptDNA yielding two and one aadA$^{au}$ copies per ptDNA, respectively. Double aadA$^{au}$ gene dosage in the Nt-pKMS8 plants was expected to yield a more robust aurea phenotype. The aadA$^{au}$ transgenes are schematically shown in FIG. 2a; the 5'-regulatory sequences are given in FIG. 2b.

Selection of Transplastomic Clones in Culture

The objective was to develop tissue culture selectable spectinomycin resistance genes, which enable detection of transplastomic sectors in greenhouse plants by the golden leaf color. Plasmids pSS52, pKMS8, pKMS10 and pKMS12 carry only the aadA$^{au}$ gene as selective marker. Transplastomic clones were selected in bombarded leaf cultures as green shoots on the background of bleached wild type cells. The shoots obtained after bombardment with the plasmids were green and indistinguishable in appearance from shoots obtained by other aadA genes. The frequency of transplastomic clones was about the same as with other aadA genes, up to ~3 clones per bombarded sample. Thus, each of these plasmids passed the first test, providing a suitable marker for the selective recovery of transplastomic clones. We named the plants by the initial of the plant species (Nt), the plasmid name (pKMS8) and a serial number for the independently transformed clone (10), for example Nt-pKMS8-10. One and two letters were added to distinguish plants obtained from the first and second purifying regeneration, respectively, for example Nt-pKMS8-10A and Nt-pKMS8-10AL.

Detection of Transplastomic Sectors by Golden Leaf Color

Figure 3:
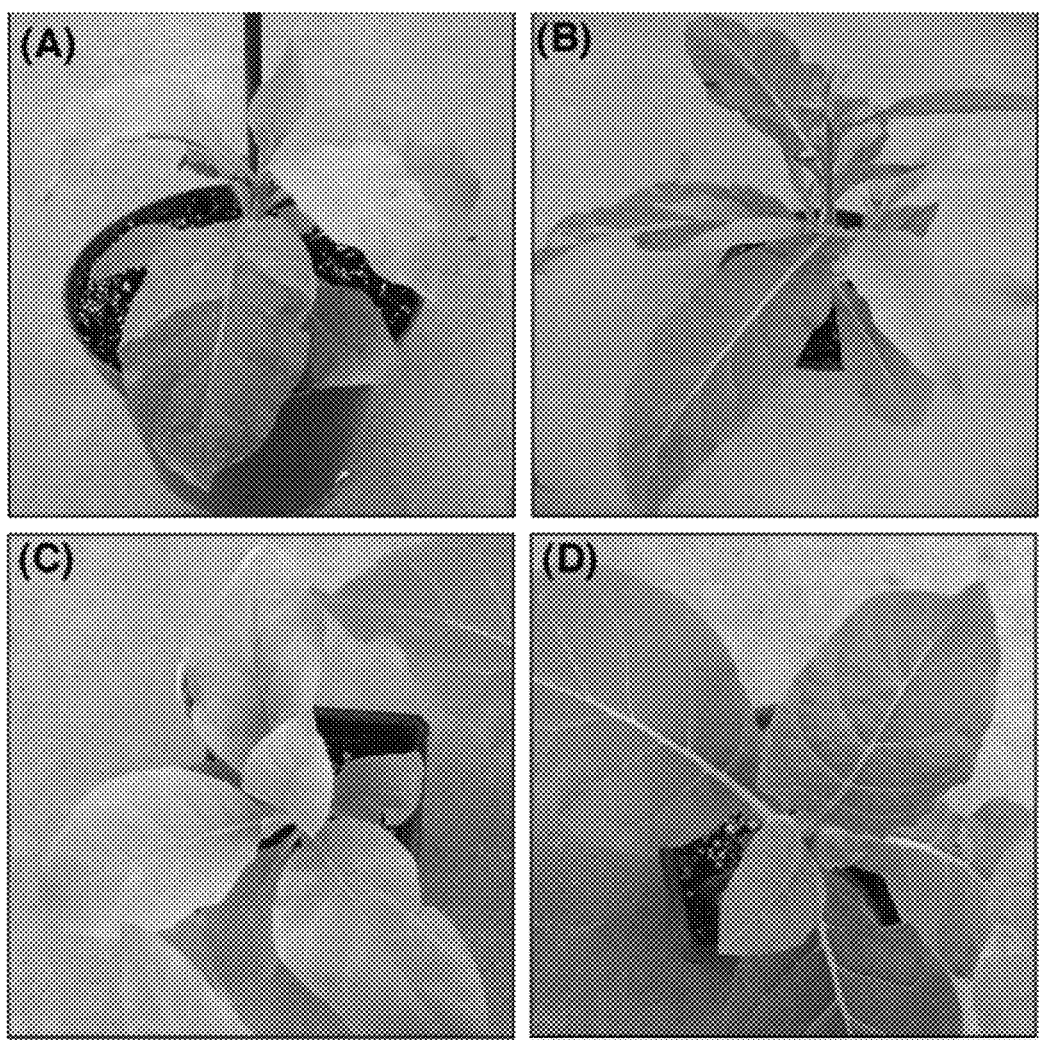
FIG. 3 The aurea phenotypes of greenhouse plants from the first purifying regeneration. a,b Variegated Nt-pKMS8 plants and Nt-pKMS12 plants with c aurea and d green phenotype.
Figure 5:
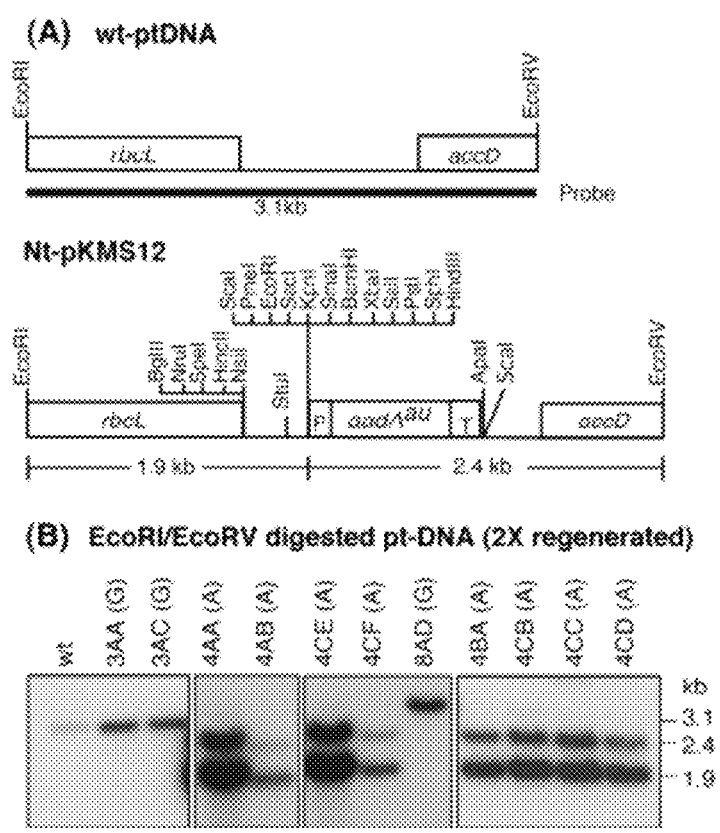
FIG. 5 DNA gel blot analyses of Nt-pKMS 12 leaves confirm that the aurea sectors contain transformed plastids. a Maps of the transformed ptDNA in Nt-pKMS12 plants and the cognate region in wild type ptDNA. b DNA gel blot analyses of leaves. The blots were probed with the 3.1 kb EcoRI-EcoRV fragment (FIG. 7a). Leaf phenotypes are given in parenthesis above the lanes. Abbreviations: A, aurea; G, green.

The second criterion for the visual marker was facile detection of transplastomic sectors in greenhouse plants by the golden leaf color. To judge the value of the aadA$^{au}$ genes as visual markers, plants were transferred to the greenhouse after the first and second purifying regeneration of the putative transplastomic clones. The first purifying regeneration involves shoot regeneration from leaves that are taken from shoots developing on bombarded leaf sections. Purifying regeneration is necessary, because ptDNA is initially transformed in only a few plastids and the shoots regenerating on the selective medium in most cases have only small transplastomic sectors. Cross-protection of wild-type cells carrying no transformed ptDNA by transplastomic tissue enables regeneration of wild type shoots from mixed, chimeric leaves. To directly assess the fraction of plants carrying transplastomic sectors, we rooted shoots from the first and second purifying regeneration and transferred the plants to the greenhouse. Among the fourteen plants derived from the first purifying regeneration of pKMS8-transformed shoots ~⅔ (nine) of the plants had variegated leaves with aurea sectors and ⅓ (five) were green; no uniformly aurea plants were obtained (Table 1) (FIG. 3). DNA gel blot analysis confirmed that the green plants carried wild type ptDNA. The green sectors of variegated leaves carried wild type, or mixed wild type and transplastomic ptDNA (T-ptDNA) while the aurea sectors contained T-ptDNA (FIG. 4). Among the 39 plants derived from the second purifying regeneration of pKMS8-transformed shoots ~40% (sixteen) had an aurea phenotype, ~45% (seventeen) had variegated leaves with aurea sectors and ~15% (six) were green (Table 1). DNA gel blot analyses in 12 out of 13 aurea plants confirmed a uniform population of T-ptDNA (FIG. 4b). A similar trend was observed among plants obtained when transformation was carried out with plasmid pKMS12: most plants from the first purifying regeneration were wild type whereas after the second purifying regeneration about half of the plants were wild type and half were homoplastomic transgenic (Table 1) (FIG. 5). The Nt-pKMS12 plants had a weaker aurea phenotype than the Nt-pKMS8 plants; this we attribute to having one copy of the aadA$^{au}$ in Nt-pKMS12 plastids and two copies in pKMS8.

Although Nt-pKMS 10 plants also had an aurea phenotype, this phenotype was weaker than those of Nt-pKMS12 plants (three and two plus marks on a subjective scale, respectively, see FIG. 2a). What complicates judging the aurea phenotype is its transient nature: the golden-yellow color is well expressed in rapidly growing leaves and disappears in older leaves that turn green as growth slows. We therefore recommend the Nt-pKMS8 vector because the aurea color of Nt-pKMS8 leaves is maintained until the first flower buds appear enabling unambiguous classification of plastid genotypes by leaf color.

The aadA$^{au}$ Gene in Nt-pKMS8 Plants Confers an Aurea Seedling Phenotype

Figure 6:
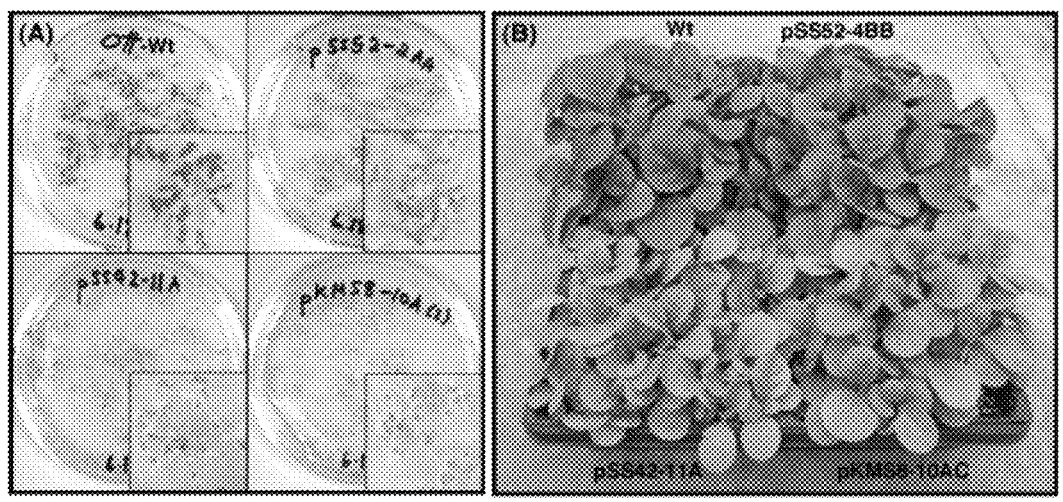
FIG. 6 The aurea phenotype of transplastomic seedlings. Shown are a two-week old seedlings germinated in sterile culture on MS medium (100 mm×20 mm Petri dish) and b 27-day old seedlings grown in greenhouse (20"×20" tray). Note that Nt-pSS52 seedlings have an aurea phenotype in sterile culture but are similar to wild type (Wt) in the greenhouse. Note also that the Nt-pSS42 and Nt-pKMS8 seedlings have comparable phenotypes in culture and in the greenhouse.

Delayed growth and vibrant aurea color facilitate distinction of aurea seedlings from wild type. We therefore germinated Nt-pSS52 and Nt-pKMS8 seed at the same time as the Nt-pSS42 seeds carrying the reference aurea bar$^{au}$ gene and wild type seed (FIG. 6). We have found that Nt-pKMS8 seedlings carrying the pKMS8 aadA$^{au}$ allele and the reference Nt-pSS42 seedlings carrying the reference bar$^{au}$ gene are affected to a similar extent with respect to delay in seed germination and greening. The two-week old Nt-pSS52 seedlings had an intermediate phenotype between the wild type and Nt-pKMS8 seedlings in culture, and were similar to wild type in the greenhouse when older (27 days).

DISCUSSION

Conversion of the aadA Spectinomycin Resistance Gene into a Visual Marker

We report here successful conversion of the aadA gene into a visual marker so that the presence or absence of the transgene can be determined by visual inspection of leaves. The aadA$^{au}$ gene is unique because it combines two roles: it is a selectable marker in tissue culture and a visual marker in plants. Selection in tissue culture is carried out as with a conventional aadA gene. Using an aurea aadA$^{au}$ instead of a conventional aadA does not shorten the time required for plastid sorting and the time required to obtain homoplastomic plants. Having the visual phenotype has the advantage that homoplastomic plants can be readily distinguished from variegated, heteroplastomic plants (FIG. 3). Such variegated, heteroplastomic plants may be present even after two cycles of plant regeneration (Table 1). These variegated plants remain undetected using the conventional aadA gene, but are readily identified using the aadA$^{au}$ gene. The only disadvantage using the aurea aadA$^{au}$ gene is that slows down development. The aurea marker is the most useful to query rare events in large populations, or when excision of the marker gene is planned from the final product (see below).

TABLE 1

Progress towards homoplastomic state in regenerated plants

| | Phenotype | | | |
|---|---|---|---|---|
| | Nt-pKMS8 | | Nt-pKMS12 | |
| | Purified 1 x | Purified 2 x | Purified 1 x | Purified 2 x |
| Green | 5 | 6 | 19 | 19 |
| Variegated | 9 | 17 | 4 | 0 |
| Aurea | 0 | 16 | 6 | 12 |

Conventional visual markers are based on mutations in plastid genes causing pigment deficiency. Pigment deficiency can be readily induced by targeted deletion of plastid genes, such as the RNA polymerase subunit-encoding rpoB gene (Allison, et al. 1996), and the rbcL (Kanevski and Maliga 1994) and psbA (Baena-Gonzales, et al. 2003) photosynthetic genes. These pigment mutants are difficult to handle because they are unable to grow without supporting wild-type tissue. The interference by the aadA$^{au}$marker produces plants with reduced growth and a distinct color, but maintains a wild-type gene set and the capacity for photosynthesis. More importantly, when the aurea marker is removed, normal growth rate signaling the fully functional status of plastids is restored (see below). The new marker gene will take over the role of the aurea bar$^{au}$ gene, which induces a similar visual phenotype, but is not selectable in culture.

Genes conferring kanamycin resistance to plastids, such as neo and aph(3')IIa, are selectable in tissue culture (Caner, et al. 1993, Huang, et al. 2002, Lutz, et al. 2004). A mild form of an aurea phenotype was first discovered as a phenotype caused by a neo gene variant encoded in plasmid pHK33 (Kuroda and Maliga 2002). We did not consider engineering neo to enhance its aurea phenotype because inefficient translation from the clpP1 leader yielded only low levels (~0.26%) of the encoded NPTII, considered too low for kanamycin selection in culture. In contrast, low levels (<1%) of AAD, the aadA gene product, are sufficient for the recovery of transplastomic clones (Sinagawa-Garcia, et al. 2009).

A salient feature of the aurea phenotype conferred by aadA$^{au}$ is its transient nature: it is readily detectable in young seedlings, presumably reflecting the high demand for the ClpP 1 protease subunit (Kuroda and Maliga 2002) that subsides as growth slows and, by the time the plants are flowering, wild type pigmentation is restored. Consequently, to satisfy the demand for rapid growth, regular fertilization is critical when scoring seedlings for the aurea phenotype.

The aadA$^{au}$ Gene Enables Visual Assessment of the Homoplastomic State

We took the opportunity of the visual phenotype of our new transplastomic clones to assess the progress towards achieving the homoplastomic state, when each cell carries a uniform population of transformed ptDNA. From the data it became apparent that: (i) a significant fraction of shoots can be wild type even in the second purifying regeneration cycle and that (ii) the aurea phenotype is a reliable predictor of plastid genotype. Induction of a new shoot apical meristem from one cell is the opportunity to create a new shoot apex with a uniform ptDNA population.

Therefore, regeneration of a new shoot apex is essential to obtain genetically uniform plants because cells with different plastid types may be locked in different developmental layers of the shoot apex. Genetically stable, homoplastomic plants are obtained when the two to three long-term stem cells in each of the three layers carry the same plastid types (Lutz and Maliga 2008). To allow time for plastid sorting, we normally take older leaves for purifying regeneration from well-developed shoots. If plastid sorting is advanced and the leaves contain homoplastomic sectors of transplastomic and wild type cells, the regenerated plants will be either transplastomic or wild type. Indeed, the variegated category was absent in the twice-purified Nt-pKMS 12 plants that were either homoplastomic or wild type, as expected (Table 1). However, heteroplastomic plants are obtained in significant numbers in the second purifying selection if the first purifying selection was initiated too early, as in the Nt-pKMS8 cultures.

Applications of Aurea Plastid Genes

Because the plants are viable, the aurea markers are useful to query rare events in large populations. The recovery of rare events depends on, whether or not small green sectors can be identified on the aurea background. The vectors described here do not carry sequences for marker excision, thus are not suitable to test the restoration of green phenotype, due to excision of aadA$^{au}$. However, study of plastid segregation reported here with the aadA$^{au}$ gene yielded results that are similar to those obtained with the bar$^{au}$ gene. The examples for past application of the bar$^{au}$ gene include the study of plastid sorting in heteroplastomic cells, where heteroplastomic cells were obtained by excision mediated by a site-specific recombinase. The study led to the conclusion that ptDNA in a regenerating tobacco shoot derive from a small number of copies selected through a stochastic process. Thus, formation of heteroplastomic plants during shoot regeneration is not necessarily the rule because ptDNA in a regenerating shoot derives from a small number of ptDNA copies and even rare plastid types may sort out to yield a homoplastomic plant (Lutz and Maliga 2008). The bar$^{au}$ gene was also useful to test plastid genome stability when the marker gene was flanked by direct repeats that are target sites for site-specific recombinases. In this study, the bar$^{au}$ gene was flanked by loxP or attP/attBtarget sites that are recognized by the Cre and phiC31 site specific recombinases. Loss of the bar$^{au}$ gene could have been detected by formation of green seedlings among the aurea plantlets. Because in a population of ~40,000 seedlings no green plants were obtained in which loss of the bar$^{au}$ gene was due to recombination via the recombinase target sites, it was concluded that the repeats required for marker excision are too short to facilitate deletion of the marker genes at a measurable rate (Tungsuchat-Huang, et al. 2010). When the bar$^{au}$ gene marker is removed, green pigmentation and normal growth rate are restored so that marker-free plants can be identified as sectors or in the seed progeny. Plants with target site flanked bar$^{au}$ marker genes were useful to explore in planta marker excision by *Agrobacterium* injection so that seed of plastid marker-free plants could be obtained without using tissue culture. See Example II. Expected uses of the aurea aadA$^{au}$ gene are the same as of the bar$^{au}$ gene with the additional advantage that the transplastomic clones can be obtained by direct selection for the aadA$^{au}$ gene.

References for Example I

Allison L A, Simon L D, Maliga P (1996) Deletion of rpoB reveals a second distinct transcription system in plastids of higher plants. EMBO J 15: 2802-2809.

Apel W, Bock R (2009) Enhancement of carotenoid biosynthesis in transplastomic tomatoes by induced lycopene-to-provitamin A conversion. Plant Physiol 151: 59-66. doi: 10.1104/pp. 109.140533

Baena-Gonzales E, Allahverdieva Y, Svab Z, Maliga P, Josse E M, Kuntz M, Mäenpää P, Aro E M (2003) Deletion of the tobacco plastid psbA gene triggers post-transcriptional up-regulation of thylakoid-associated terminal oxidase (PTOX) and the NAD(P)H complex. Plant J 35: 704-716. doi: 10.1046/j.1365-313X.2003.01842.x Barone P, Zhang X H, Widholm J M (2009) Tobacco plastid transformation using the feedback-insensitive anthranilate synthase [alpha]-subunit of tobacco (ASA2) as a new selectable marker. J Exp Bot 60: 3195-3202. doi: 10.1093/jxb/erp160

Bock R (2007) Plastid biotechnology: prospects for herbicide and insect resistance, metabolic engineering and molecular farming. Curr Opin Biotechnol 18: 100-106. doi: 10.1016/j.copbio.2006.12.001

Caner H, Hockenberry T N, Svab Z, Maliga P (1993) Kanamycin resistance as a selectable marker for plastid transformation in tobacco. Mol Gen Genet 241: 49-56.

Church G M, Gilbert W (1984) Genomic sequencing. Proc Natl Acad Sci USA 81: 1991-1995.

Daniell H, Chebolu S, Kumar S, Singleton M, Falconer R (2005) Chloroplast-derived vaccine antigens and other therapeutic proteins. Vaccine 23: 1779-1783.doi: 10.1016/j.vaccine.2004.11.004

Huang F C, Klaus S M J, Herz S, Zuo Z, Koop H U, Golds T J (2002) Efficient plastid transformation in tobacco using the aphA-6 gene and kanamycin selection. Mol Genet Genomics 268: 19-27. doi: 10.1007/s00438-002-0738-6

Kanevski I, Maliga P (1994) Relocation of the plastid rbcL gene to the nucleus yields functional ribulose-1,5-bisphosphate carboxylase in tobacco chloroplasts. Proc Natl Acad Sci USA 91: 1969-1973.

Kittiwongwattana C, Lutz K A, Clark M, Maliga P (2007) Plastid marker gene excision by the phiC31 phage site-specific recombinase. Plant Mol Biol 64: 137-143. doi: 10.1007/s11103-007-9140-4

Kuroda H, Maliga P (2001a) Complementarity of the 16S rRNA penultimate stem with sequences downstream of the AUG destabilizes the plastid mRNAs. Nucleic Acids Res 29: 970-975.

Kuroda H, Maliga P (2001b) Sequences downstream of the translation initiation codon are important determinants of translation efficiency in chloroplasts. Plant Physiol 125: 430-436.

Kuroda H, Maliga P (2002) Over-expression of the clpP 5'-UTR in a chimeric context causes a mutant phenotype suggesting competition for a clpP-specific RNA maturation factor in tobacco chloroplasts. Plant Physiol 129: 1600-1606. doi: 10.1104/pp.004986

Li W, Ruf S, Bock R (2011) Chloramphenicol acetyltransferase as selectable marker for plastid transformation. Plant Mol Biol 10.1007/s11103-010-9678-4

Lutz K, Corneille S, Azhagiri A K, Svab Z, Maliga P (2004) A novel approach to plastid transformation utilizes the phiC31 phage integrase. Plant J 37: 906-913.

Lutz K A, Azhagiri A K, Tungsuchat-Huang T, Maliga P (2007) A guide to choosing vectors for transformation of the plastid genome of higher plants. Plant Physiol 145: 1201-1210. doi: 10.1104/pp. 107.106963

Lutz K A, Knapp J E, Maliga P (2001) Expression of bar in the plastid genome confers herbicide resistance. Plant Physiol 125: 1585-1590.

Lutz K A, Maliga P (2007) Transformation of the plastid genome to study RNA editing. Methods Enzymol 424: 501-518. doi: 10.1016/S0076-6879(07)24023-6

Lutz K A, Maliga P (2008) Plastid genomes in a regenerating tobacco shoot derive from a small number of copies selected through a stochastic process. Plant J 56: 975-983. doi: 10.1111/j.1365-313X.2008.03655.x Lutz K A, Svab Z, Maliga P (2006) Construction of marker-free transplastomic tobacco using the Cre-loxP site-specific recombination system. Nat Protocols 1: 900-910. doi:10.1038/nprot.2006.118

Madoka Y, Tomizawa K I, Mizoi J, Nishida I, Nagano Y, Sasaki Y (2002) Chloroplast transformation with modified accD operon increases acetyl-Co-A carboxylaase and causes extension of leaf longevity and increase in seed yield in tobacco. Plant and Cell Physiology 43: 1518-1525.

Maliga P (2004) Plastid transformation in higher plants. Ann Rev Plant Biol 55: 289-313. doi: 10.1146/annurev.arplant.55.031903.141633

Murashige T, Skoog F (1962) A revised medium for the growth and bioassay with tobacco tissue culture. Physiol Plant 15: 473-497.

Murray M G, Thompson W F (1980) Rapid isolation of high molecular weight plant DNA. Nucleic Acids Res 8: 4321-4325.

Raubeson L A, Jansen R K (2005) Chloroplast genomes of plants. In: Henry R J (ed) Diversity and Evolution of Plants—Genotypic and Phenotypic Variation in Higher Plants. CABI Publishing, Wallingford, UK, pp. 45-68.

Sharwood R E, von Caemmerer S, Maliga P, Whitney S M (2008) The catalytic properties of hybrid rubisco comprising tobacco small and sunflower large subunits mirror the kinetically equivalent source Rubiscos and can support tobacco growth. Plant Physiol 146: 83-96. doi: 10.1104/pp.107.109058

Sinagawa-Garcia S R, Tungsuchat-Huang T, Paredes-Lopez O, Maliga P (2009) Next generation synthetic vectors for transformation of the plastid genome of higher plants. Plant Mol Biol 70: 487-498. doi: 10.1007/s11103-009-9486-x Sprengart M L, Fuchs E, Porter A G (1996) The downstream box: an efficient and independent translation initiation signal in *Escherichia coli*. EMBO J 15: 665-674.

Sriraman P, Silhavy D, Maliga P (1998) The phage-type PclpP-53 plastid promoter comprises sequences downstream of the transcription initiation site. Nucleic Acids Res 26: 4874-4879.

Suzuki J Y, Sriraman P, Svab Z, Maliga P (2003) Unique architecture of the plastid ribosomal RNA operon promoter recognized by the multisubunit RNA polymerase (PEP) in tobacco and other higher plants. Plant Cell 15: 195-205.

Svab Z, Maliga P (1993) High-frequency plastid transformation in tobacco by selection for a chimeric aadA gene. Proc Natl Acad Sci USA 90: 913-917.

Tungsuchat-Huang T, Sinagawa-Garcia S R, Paredes-Lopez O, Maliga P (2010) Study of plastid genome stability in tobacco reveals that the loss of marker genes is more likely by gene conversion than by recombination between 34-bp loxP repeats. Plant Physiol 153: 252-259. doi: 10.1104/pp.109.152892

Wakasugi T, Tsudzuki T, Sugiura M (2001) The genomics of land plant chloroplasts: gene content and alteration of genomic information by RNA editing. Photosynth Res 70: 107-118. doi: 10.1023/A:1013892009589

Whitney S M, Andrews T J (2001) Plastome-encoded bacterial ribulose-1,5-bisphosphate carboxylase/oxygenase (Rubisco) supports photosynthesis and growth of tobacco. Proc Natl Acad Sci USA 98: 14738-14743.

Whitney S M, Andrews T J (2003) Photosynthesis and growth of tobacco with substituted bacterial rubisco mirror the properties of the introduced enzyme. Plant Physiol 133: 287-294. doi: 10.1104/pp.103.026146

Ye G N, Colburn S, Xu C W, Hajdukiewicz P T J, Staub J M (2003) Persistance of unselected transgenic DNA during a plastid transformation and segregation approach to herbicide resistance. Plant Physiol 133: 402-410.

Example II

Visual Marker and *Agrobacterium*-Delivered Recombinase Enable the Manipulation of the Plastid Genome in Greenhouse-Grown Tobacco Plants Successful manipulation of the plastid genome (ptDNA) so far has been carried out in tissue culture cells, a limitation that prevents plastid transformation being applied in major agronomic crops. Our objective is to develop a tissue-culture independent protocol that enables manipulation of plastid genomes directly inplants yielding genetically stable seed progeny. We report that in planta excision of a plastid aurea bar gene (bar$^{au}$) is detectable in greenhouse-grown plants by restoration of the green pigmentation in tobacco leaves. The P1 phage Cre or PhiC31 phage Int site-specific recombinase was delivered on the *Agrobacterium* T-DNA injected at the axillary bud site, resulting in the excision of the target-site flanked marker gene. Differentiation of new apical meristems was forced by decapitating the plants above the injection site. The new shoot apex differentiating at the injection site contained marker-free plastids in 30% to 40% ofthe injected plants, of which 7% transmitted the marker-free plastids to the seed progeny. The success of obtaining seed with marker-free plastids depended on repeatedly forcing shoot development from axillary buds, a process that was guided by the size and position of green sectors in the leaves. The success of in planta plastid marker excision proved that manipulation of the plastid genomes is feasible within an intact plant. Extension of the protocol to in planta plastid transformation depends on the development of new protocols for the delivery of transforming DNA encoding visual markers.

While the use of CRE/lox and phi3/att integrase/recombinases are exemplified herein, other recombinases and their cognate excision site sequences known by the skilled artisan and are encompassed within the scope of the present invention. See for example Table I in PCT/US04/06492.

The following materials and methods are provided to facilitate the practice of Example II.

Plant Materials and Growth Conditions

Figure 7:
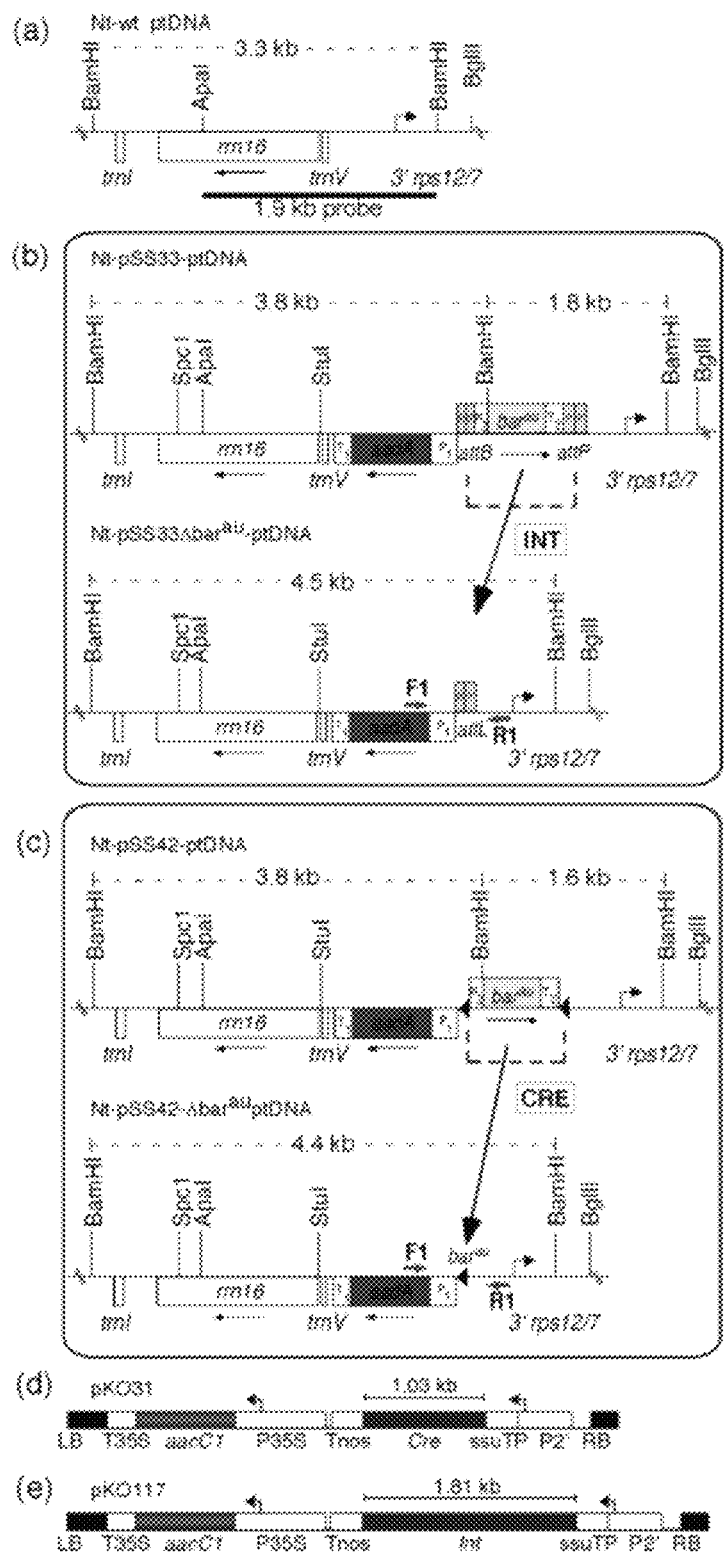
FIG. 7 Visual system to detect recombinase-mediated plastid marker excision. (a) Engineered region in the wild type ptDNA. Shown are the rrn16,trnV and 3'-rps12plastid genes and relevant restriction endonuclease cleavage sites. (b) Nt-pSS33 transplastome with aadA spectinomycin resistance gene and bar$^{au}$ flanked with the attB-attP target sites and the product of bar$^{au}$ excision byInt. Cassettes driving the expression of transgenes are: P1 and T1, the psbA plastid gene promoter and terminator; and P2 is the PrrnPclpP promoter and T2 the rbcL terminator. F1 and R1 mark the position of primers to sequence the recombinant target site. (c) Nt-pSS42 transplastome with the aadA gene and bar$^{au}$ flanked with loxP target sites and the product of bar$^{au}$ excision byCre. For further explanation see caption to FIG. 1b. (d,e) T-DNA region in plasmids pKO31 and pKO117 with a plastid-targeted Cre and Int, respectively. The recombinases are expressed in the P2 promoter-Tnos terminator cassettes. Shown are also the left and right T-DNA borders and the aacC1 plant-selectable gentamycin resistance gene.

Nt-pSS33-1AA and Nt-pSS33-1BA tobacco plants used in this study carry a plastid-encoded spectinomycin resistance (aadA) gene and an aurea bar$^{au}$ plastid marker flanked with the 215-bp attP and 54-bp attB target sites (FIG. 7b). The attP and attB sites are recognized by the phiC31 phage Int recombinase. Nt-pSS42-11A and Nt-pSS42-18B are similar transplastomic plants, except that the bar$^{au}$ is flanked with 34-bp loxP sites recognized by the P1 phage Cre recombinase (FIG. 7c). These transplastomic *Nicotiana tabacum* cv. Petit Havana (tobacco) plants have been described (Tungsuchat-Huang et al. 2010).

The plants for injection were grown in 7.5 inches plastic pots with supplemental lighting (16 hours daylight) in the greenhouse until 10-12 inches tall in Pro-Mix general purpose growing medium Code 0432 (Premier Horticulture Inc., Quakertown, Pa.).

To identify seedlings with marker-free plastids, 200 to 300 seeds were germinated in 10"×10" square flat trays (Tungsuchat-Huang et al. 2010). The seedling phenotype was scored after 4 to 5 weeks as dark green or aurea.

*Agrobacterium* Injection

Buds were removed and then each node was injected at the bud site with *Agrobacterium tumefaciens*strain EHA101 carrying binary plasmids pKO31 or pKO117. Plasmid pKO31 carries in its T-DNA a plastid-targeted Cre recombinase and a plant-selectable gentamycin resistance (aacC1) gene (FIG. 7d) (Corneille et al. 2003). Plasmid pKO117 is a similar binary plasmid, other than it encodes a plastid targeted Int (FIG. 7e) (Lutz et al. 2004). Agrobacterium suspension cells were prepared as described (Lutz et al. 2006a, Lutz et al. 2006b). Briefly, Agrobacterium carrying the binary plasmids was inoculated in 100 ml YEB medium supplemented with 100 mg/L spectinomycin and 50 mg/L kanamycin and grown overnight at 27° C. 1 ml of the overnight culture was transferred into fresh YEB medium containing 10 mM MES, pH-adjusted to 5.6, 20 µM acetosyringone, 100 mg/L spectinomycin and 50 mg/L kanamycin and grown overnight at 27° C. The bacterial cultures were sedimented by centrifugation and resuspended in MMA medium (supplemented with 200 µM acetosyringone) to a final $OD_{600}$=2.4 and incubated at room temperature for at least 2-3 hours.

Prior to injection the Nt-pSS33 or Nt-pSS42 plants were heavily watered, then the shoots were decapitated and all buds were removed. Each node was then injected at the bud site at least three times using a 3-mL syringe with a 25G×1½ inches needle (Becton Dickinson, Franklin Lakes, N.J.). After the injection the plants were covered with plastic sheets to prevent desiccation and stored in low light at 25° C.-30° C. for 24 hours before moving them back into the greenhouse.

DNA Gel-Blot Analyses and Sequencing of PCR Products

Total cellular DNA was prepared from leaf tissue by the CTAB protocol (Murray et al. 1979). DNA gel-blot analysis was performed as described. Total cellular DNA was digested with the BamHI restriction enzyme and separated by electrophoresis in 0.8% agarose gel. The DNA was transferred to Hybond-N membranes (GE Healthcare, Piscataway, N.J.) and hybridized with a random-primed, $P^{32}$-labeled rrn16 plastid targeting-region probe (ApaI-BamHI fragment) (Svab and Maliga 1993).

For sequencing the recombinant target sites, the intergenic region between rrn16 and 3'rps12/7 gene was amplified from total cellular DNA with primer F1/#816 (5'-GGCTTCAG-GCCGCCATCCACT-3', SEQ ID NO: 4) and R1/#T01 (5'-GTAGTTAATGGTAGGGTTACC-3', SEQ ID NO: 5) and sequenced with primer R1/#T01. The position of the F1 and R1 primers is shown in FIG. 7b,c.

Testing Leaf Sections for Gentamycin Resistance

Leaves from greenhouse plants were surface sterilized with 10× diluted Clorox bleach (0.6% sodium hypochlorite; 3 min) in a glass tray and then washed three times with sterile distilled water. The sterile leaves were blotted on a Whatman filter paper to absorb the excess water, then cut into 1 cm×1 cm squares and placed on RMOP media supplemented with 100 mg/L gentamycin (Carrer et al. 1990). The number of tested sections depended on sector size.

To test the feasibility of in planta plastid genome manipulation, we decided to excise the $bar^{au}$ gene with the P1 phage Cre or PhiC31 phage Int site-specific recombinase. Useful for this study were the transplastomic plants in which the $bar^{au}$ gene is flanked by recombinase target sites (Tungsuchat-Huang et al. 2010). The success of the project depended on obtaining shoots in which the marker-free plastids were at the leaf margins, indicating the presence of marker-free plastids in the second layer of the shoot apex, the source of germline cells in plants (Poethig 1989). To force regeneration of shoots from Agrobacterium-transformed cells, we decapitated the plants, removed the top two or three axillary buds, and injected the bud site with Agrobacterium.

Results

System for Detection of Recombinase-Mediated Plastid Marker Excision

We have designed a sensitive system to detect plastid marker excision in plants by the change of leaf color. The presence of the $bar^{au}$ gene confers a golden-yellow (aurea) leaf color due to interference with the expression of the plastid clpP gene (Kittiwongwattana et al. 2007). When the $bar^{au}$ marker gene is excised, green pigmentation is restored, providing a readily detectable visual phenotype for marker excision. In the Nt-pSS33 plastids the $bar^{au}$ geneis flanked by attB and attP sites (FIG. 7b) that arerecognized by Int, the PhiC31 phage site-specific recombinase (Tungsuchat-Huang et al. 2010). In the Nt-pSS42 plastids the visual marker gene is flanked by loxP sites (FIG. 7c), which are the targetssites of the P1 phage recombinase (Tungsuchat-Huang et al. 2010).

The recombinase genes were expressed from the T-DNA region of Agrobacterium binary transformation vectors: plasmid pKO31 (Corneille et al. 2003) and pKO117 (Lutz et al. 2004) encode a plastid-targeted Cre and Int, respectively (FIG. 7d, e). Plastid targeting was facilitated by fusing the recombinases with the rubisco small subunit transit peptide and five (pKO31) or 22 (pKO117) amino acids of the mature rubisco small subunit. Both vectors carry a gentamycin resistance (aacC1) gene. We used gentamycin resistance to distinguish recombinase delivery from a transiently expressed or stably integrated T-DNA by the absence or presence of the gentamycin resistance marker gene (Lutz et al. 2006a).

Green Sectors Form on the Aurea Leaves After Agrobacterium Injection

Figure 8:
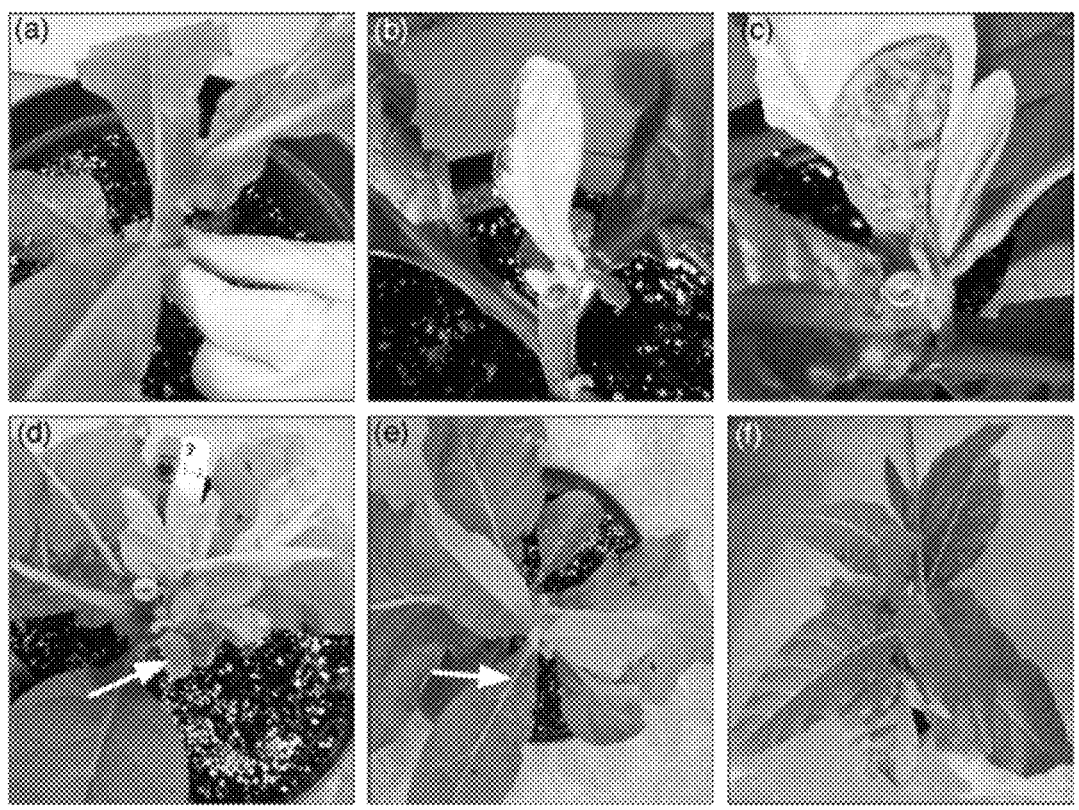
FIG. 8 Green sectors form in aurea leaves after Agrobacterium injection. (a) Agrobacterium injection of the aurea Nt-pSS42 tobacco stem, at the bud site. Note that only the rapidly developing, young leaves have the aurea color and the older leaves shown here turn green. (b-d) Excision of the bar$^{au}$ gene by Cre in the Nt-pSS42 plants yields a few (b) or many (c,d) dark green sectors (arrow). (e) Half of the shoot apex of Layer 2 is dark green in Nt-pSS33 plant injected with Agrobacterium carrying plasmid pKO117. (d) Forcing shoot development from the axillary bud in FIG. 2e by decapitating shoot above the dark green leaf (arrow in FIG. 2e) yields uniform dark green shoot.

De novo transformation of tissue culture cells with a plastid-targeted recombinase is the most common protocol to obtain marker-free transplastomic plants (Lutz and Maliga 2007). We report here a novel, second de novo transformation approach by directly transforming the germline cells in the shoot apex by injected Agrobacterium cells. During the injection the needles destroyed the shoot apex, thereby forcing the regeneration of new shoot meristems from the injected tissue (FIG. 8a). New shoots with dark-green sectors on the aurea leaf background appeared one to two weeks after the injection. The dark green sectors in some of the leaves were localized to the leaf margin of a single leaf (FIG. 8b), in others many dark-green excision sectors formed in the different developmental layers, but excision was still restricted to a single leaf (FIG. 8c,d). Localization of the sectors to a single leaf suggests that excision took place in the leaf primordia (Poethig 1989). In other plants dark-green sectors were present in multiple leaves indicating that the cells carrying $bar^{au}$ marker-free plastids were present in the shoot apex. The size of the dark-green sectors in some shoots was sizable, with half of the shoot apex made up of cells with dark-green plastids. The dark green cells in the variegated leaf in FIG. 8e derive from Layer 2 of the shoot apex (Poethig 1989). When the shoot was decapitated above the green leaf (arrow), the shoot developing from the axillary bud had a uniform dark-green color, with dark green plastids in both Layer 2 and 3 (FIG. 8f).

In two experiments a total of 147 plants were injected (Table 2). Out of 73 Cre-injected plants 32 (43%) developed shoots with green sectors, out of which 12 (16%) had dark green plastids in Layer 2 of the leaf (Table 2). Cells in Layer 2 of the leaf have the same genotype as the germline cells in the shoot apex indicating the potential for seed transmission (Poethig 1989), Injection of Nt-pSS33 plants with Int yielded plants with dark-green sectors at a similar frequency. Out of 74 Int-injected plants 20 plants (27%) developed shoots with green sectors, out of which 9 (12%) carried cells with marker-free plastids at the leaf margin indicating potential for seed transmission (Table 2).

TABLE 2

Frequency of in planta plastid marker excision in Agrobacterium-injected plants

| Experiment | Recombinase | No. of injected plants | No. of plants with sectors | No. of plants with green plastids in germline |
|---|---|---|---|---|
| I | Cre | 50 | 19 | 3 |
|  | Int | 50 | 18 | 8 |
| II | Cre | 23 | 13 | 9 |
|  | Int | 24 | 2 | 1 |
| I + II | Cre | 73 | 32 (43%) | 12 (16%) |
|  | Int | 74 | 20 (27%) | 9 (12%) |

DNA Analysis Confirms $bar^{au}$ Excision in the Green Sectors

Excision of $bar^{au}$ in the green sectors of variegated leaves was confirmed by DNA gel blot analyses using the plastid targeting region (rrn16) probe (FIG. 7a) (Kittiwongwattana et al. 2007). In the transplastomic aurea Nt-pSS42 plants the rrn16 targeting region probe detects 3.8-kb and 1.6-kb fragments whereas Cre excision yields a 4.4-kb $bar^{au}$-lacking fragment (FIG. 7c). A DNA gel blot analysis in the green sectors of injected Nt-pSS42 plants indicates a mixed $bar^{au}$-containing and $bar^{au}$-free ptDNA population (FIG. 9a). A similar analysis of the green sectors was carried out in the Agrobacterium-injected Nt-pSS3 plants. In the transplastomic aurea Nt-pSS3 plants the rrn16 targeting region probe detects 3.8-kb and 1.8-kb fragments and Int excision yields a 4.5-kb ptDNA fragment lacking $bar^{au}$ (FIG. 7b). A DNA gel blot analysis in the nine dark-green sectors indicates mixed $bar^{au}$-containing and $bar^{au}$-free ptDNA population (FIG. 9a). The ratio of $bar^{au}$ containing and lacking fragments is variable. In two sectors (number 2 and 4) the $bar^{au}$ containing 3.8-kb fragment is almost absent.

Excision of $bar^{au}$ was confirmed by sequencing PCR-amplified excision products directly from the green sectors of the aurea leaves. The primers complementary to aadA and the ptDNA targeting region (F1 and R2 in FIG. 7b,c) selectively amplified the excision product. DNA sequence of the fragments from 14 Nt-pSS42 plants and 9 Nt-pSS33 green sectors revealed only the aadA gene promoter, one recombinant target site (loxPor attL) and the plastid targeting region, as predicted.

Figure 10:
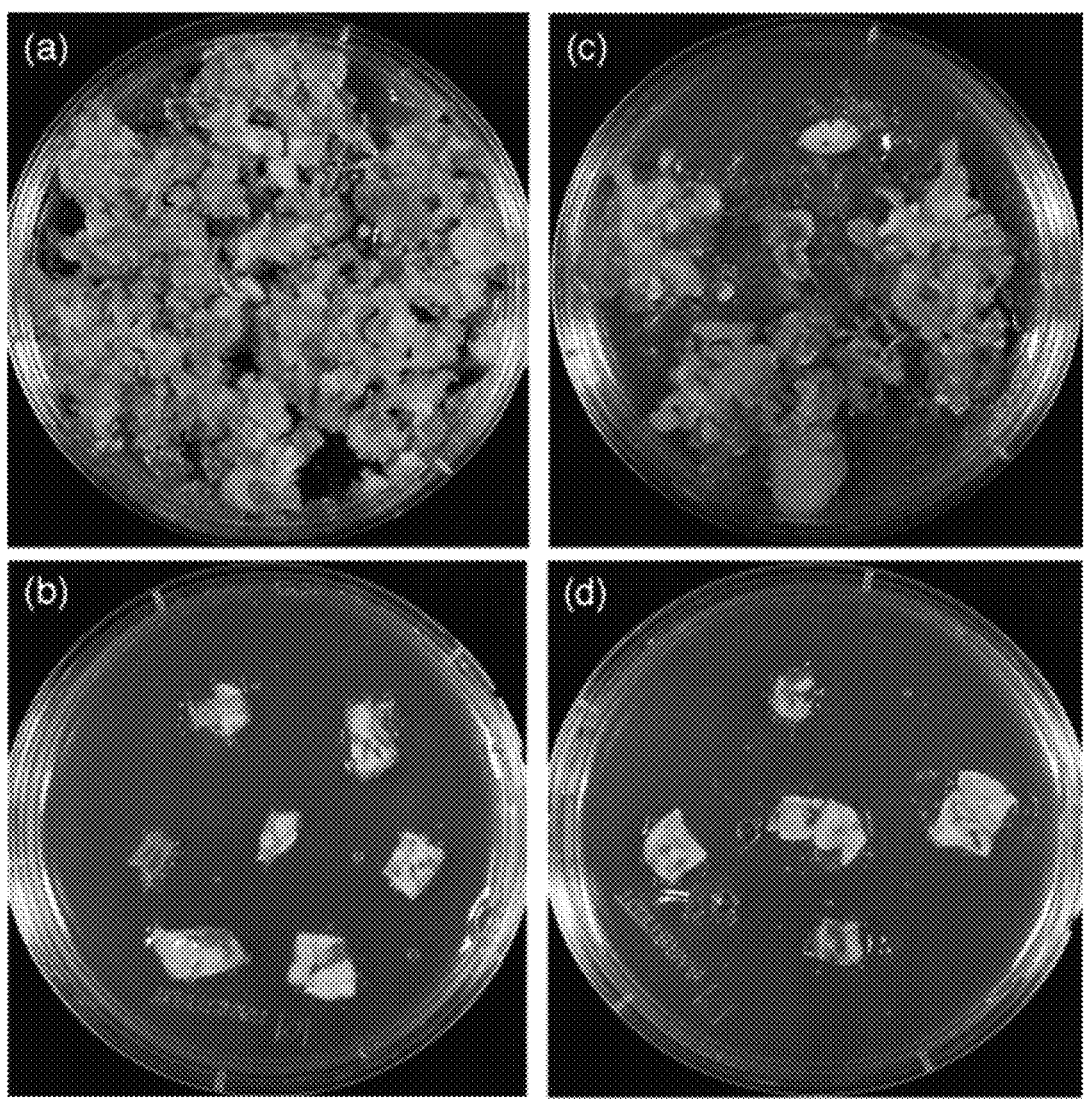
FIG. 10 Testing gentamycin resistance in green leaf sectors. (a) Formation of green callion the selective medium indicates gentamycin resistance and integration of recombinase gene. (b) Sensitivity to gentamycin suggests bar$^{au}$ excision by transiently expressed recombinase. (c) Segregation for gentamycin resistance in different explants of the same sector suggests excision by both mechanisms. (d) Wild-type gentamycin sensitive cultures.

Plastid Marker Excision is by Transiently Expressed or Stably Integrated Recombinase Genes Excision of the plastid marker may be carried out by a transiently expressed or by a stably integrated recombinase. Transient or stable delivery can be distinguished by the absence or presence of the gentamycin resistance gene in the green sectors that are adjacent to the recombinase genes in the T-DNA (FIG. 7d,e). To determine the transient or stable mode of delivery, we tested the gentamycin resistance phenotype of the green sectors by culturing them on a medium containing gentamycin. Formation of green calli on the selective medium indicates gentamycin resistance and brown necrotic tissue gentamycin sensitivity (FIG. 10).

Testing 1 $cm^2$ dark green leaf sections revealed that eleven of the green sectors were gentamycin sensitive indicating marker excision by a transiently expressed recombinase, whereas explants from four sectors were gentamycin resistant indicating the presence of an integrated recombinase (T-DNA) copy (Table 3). Segregation for gentamycin resistance in eight of the 23 green sectors suggests marker excision by both a transiently expressed and stably integrated recombinase (FIG. 10c).

TABLE 3

Testing recombinase integration by expression of linked gentamycin resistance gene

| Nt-pSS42-11A/Cre | | | | Nt-pSS33-BA/Int | | | |
|---|---|---|---|---|---|---|---|
| Leaf explants[a] | Gent-R[b] | Gent-S[c] | Total | Leaf explants[a] | Gent-R[b] | Gent-S[c] | Total |
| 1-1.1 | 1 | 6 | 7 | 3-1 | 3 | 4 | 7 |
| 1-1.2 | 2 | 5 | 7 | 3-2 | 0 | 6 | 6 |
| 1-1.4 | 0 | 3 | 3 | 3-3 | 0 | 5 | 5 |
| 1-1.5 | 1 | 3 | 4 | 3-5 | 3 | 0 | 3 |
| 1-1.8 | 0 | 2 | 2 | 3-9 | 3 | 2 | 5 |
| 1-1.9 | 1 | 3 | 4 | 3-10 | 0 | 7 | 7 |
| 1-1.10 | 7 | 0 | 7 | 4-1 | 3 | 0 | 3 |
| 1-1.11 | 1 | 5 | 6 | 4-5 | 3 | 0 | 3 |
| 1-1.12 | 0 | 2 | 2 | 4-9 | 6 | 3 | 9 |
| 1-1.13 | 0 | 5 | 5 | | | | |
| 1-4 | 0 | 2 | 2 | | | | |
| 2-2 | 0 | 7 | 7 | | | | |
| 2-7 | 0 | 2 | 2 | | | | |
| 2-12 | 0 | 2 | 2 | | | | |

Figure 11:
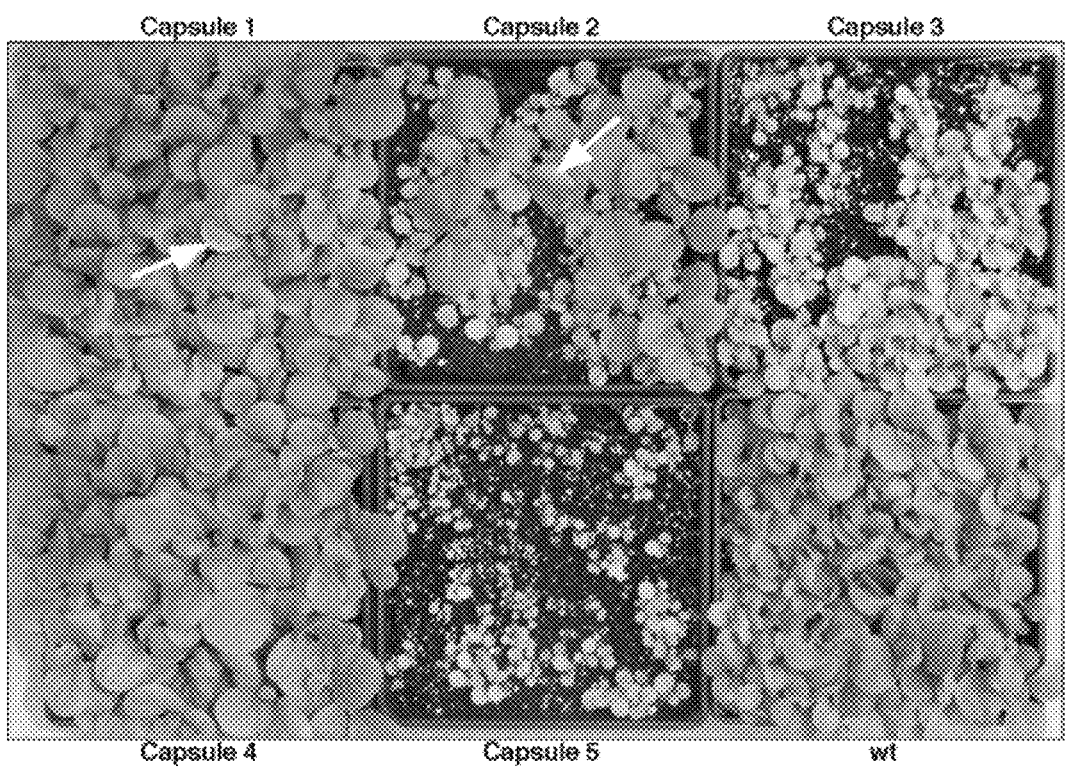
FIG. 11 Seed transmission of the green (bar$^{au}$-free) plastids to the Nt-pSS33-1BA-I3-2 seed progeny. Seed from individual capsules (1-5) were sown in trays. Green and variegated seedlings grew faster than their aurea sibs. Seedling DNA analyses (FIG. 3b) confirmed bar$^{au}$excision. White arrow in Capsule 2 seedlings points to variegated leaf. For reference, wild-type (wt) seedlings are also shown.
Figure 12:
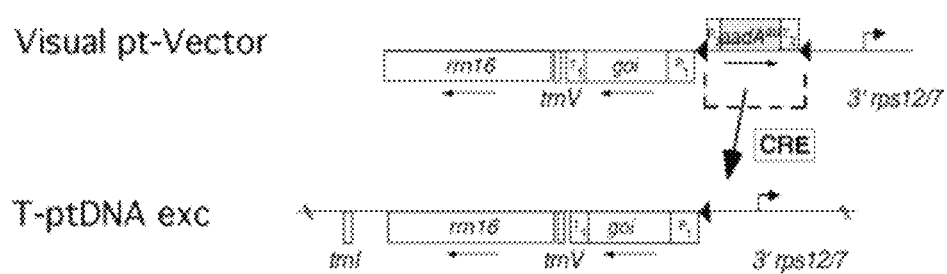
FIG. 12. In planta plastid transformation vector with the bar$^{au}$ visual marker gene. On top is shown the vector with the bar$^{au}$ gene flanked by loxP sites (triangles) and a gene of interest (goi) and the left targeting region encoding the rrn16 and trnV plastid genes and the right targeting region encoding the 3'-rps12/7 operon promoter. Cassettes driving the expression of transgenes are: P1 and T1, the psbA plastid gene promoter and terminator; P2 is the PrrnPclpP promoter and T2 the rbcL terminator. Below is shown the transplastome, after excision of the bar$^{au}$ by Cre.

[a]The first digit identifies a plant; the second a leaf and the third a green sector in the leaf. For example, Explant 1-1.1 was taken from Plant No. 1, leaf No. 1 and sector No. 1.
[b]Gentamycin resistant
[c]Gentamycin sensitive Seed Transmission of Marker-Free Plastids In dicots the second leaf layer is formed from the same cells that give rise to the germline. The phenotype of the second leaf layer can be judged by the color of the leaf mesophyll cells at the leaf margins (Poethig 1989). Based on the position of the green sectors in the leaf, inheritance of the marker-free plastids was expected in 21 (14%) of the 147 injected plants. Seed transmission of the $bar^{au}$ marker-free plastids was studied in detail in eleven of the lines: nine lines injected with the Cre (I1-2, I11-1, I11-2, I11-5, I11-11, I2-2, I2-5, I2-9, I3-6) and two injected with Int (I3-2, I3-5). About 200 seeds from five capsules each was sown, and grown for four to five weeks, until the genotype of the seedlings could be judged. A typical result in FIG. 11 is shown with I3-2 seedlings (Nt-pSS33 excised with Int). Some of the capsules (number 1, 4) contained predominantly green, marker free plastids; others contained seed with pure $bar^{au}$ seedlings (number 5), or a mixed progeny (capsules 2, 3). DNA gel blot analyses confirmed absence of the $bar^{au}$ gene (FIG. 9b). Mixed $bar^{au}$-free and $bar^{au}$-containing ptDNA was detected only in the rare variegated seedlings (white arrow in FIG. 11). Out of the 11 lines tested, seed transmission of the marker-free plastids was shown in 6 lines (I11-1, I11-11, I2-9, I3-6, I3-2 and I3-5). DNA gel blot analyses indicated a homoplastomic population of marker-free plastids in the green seedlings in each of the six lines (FIG. 9b). Assuming seed transmission in 5 of the 10 non-tested clones, we expect seed transmission in 11 (7%) of the 147 injected plants.

Discussion

Plastid Marker Excision by Recombinases in Planta

Multiple protocols exist to obtain marker-free transplastomic plants including: repeat-mediated marker excision, transient cointegration, cotransformation-segregation and recombinase-mediated marker excision (Day and Goldschmidt-Clermont 2011, Lutz and Maliga 2007). Recombinase-mediated marker excision is simpler than the alternative protocols, because in this approach plastid transformation and marker excision are two separate processes. The transplastomes with target-site flanked marker genes are stable in the absence of recombinases, therefore the time of marker excision can be chosen at will (Tungsuchat-Huang et al. 2010). The marker excision protocol that we report here avoids tissue culture directly yielding marker-free seed, thus providing a facile alternative to tissue culture transformation (Corneille et al. 2001, Hajdukiewicz et al. 2001, Kittiwongwattana et al. 2007) or pollination (Corneille et al. 2001) as the means of introducing the recombinase gene. Due to transient recombinase expression, the nuclear genome remains unmodified in a significant number of marker-free events, thus eliminating the need to segregate away the recombinase gene in the seed progeny (see next section).

The process of in planta marker gene excision is relatively efficient. Plastid marker excision was obtained in 43% and 25% of the plants injected with the Cre and Int recombinases, respectively (Table 2). Out of these, about 14% of the injected shoots yielded sectors in leaf Layer 2, an indication that capsules from that branch will transmit the marker-free plastids to the seed progeny. Seed transmission of marker-free plastids was studied in eleven clones, representing plants regenerated from different injected plants: nine with the Cre and two with the Int recombinases. We identified marker-free plastids in six out of the eleven lines by testing about 200 seedlings in five capsules. The aurea bar$^{au}$ is a young leaf marker because the older leaves turn green. Thus, at the time of seed collection leaf color does not provide guidance as to which capsules to pick. Testing more capsules and individually marking capsule position relative to sectors should ensure recovery of seedlings with marker-free plastids in most clones.

DNA samples isolated from the green sectors of the injected plants were heteroplastomic, with mixed marker-free and marker-containing ptDNA (FIG. 9a). This may be due to a heteroplastomic state at the cellular level, or different ptDNA type being present in the three leaf layers. Interestingly, green marker-free seedlings in the seed progeny of these plants were homoplastomic, carrying only marker-free plastids (FIG. 9b). Apparently, plastid sorting in Layer 2 of the shoot apex, the source of germline cells, was complete by the time the flowers formed.

Some of the Clones with Marker-Free Plastids Carry no Integrated Recombinase Gene The green sectors identified cells with marker-free plastids in the leaves, but provided no information about the integrase gene encoded in the T-DNA. Information about the relative frequency of plastid marker excision by transiently expressed and stably integrated recombinase was obtained by testing gentamycin resistance in the green leaf sectors. In many of the green sectors (11 out of 23), marker excision took place by a transiently expressed recombinase, as the tissue culture derived from the green sectors was gentamycin sensitive, lacking the nuclear marker carried on the T-DNA (Table 3). Four green sectors yielded gentamycin resistant cultures indicating the presence of an integrated recombinase gene on an T-DNA. Eight green sectors segregated for gentamycin resistance indicating bar$^{au}$ excision by the expression of both transiently expressed and stably integrated recombinase genes (Table 3). Based on these data we expect that about half of lines lackan integrated recombinase in the nucleus.

We reported plastid marker excision by a transiently expressed Cre recombinase earlier using a more labor intensive protocol, random screening of plants regenerated from an Agroinfiltrated tobacco leaf (Lutz et al. 2006a). The 10% frequency of plants with marker-free plastids, and no integrated recombinase gene in the nucleus, was surprisingly high. Using a visual plastid marker in Agroinjected plants, or as a screening tool in a randomly regenerated sample, should simplify this task.

Example III

In Planta Transformation of Plastid Genomes

Our success with in planta marker excision lead us to consider what steps would enable in planta plastid transformation. There are two fundamental elements to transformation: DNA delivery and the identification of transgenic events. We developed two aurea plastid markers that are suitable for visual identification: the bar$^{au}$ (Kittiwongwattana et al. 2007) and the aadA$^{au}$ genes (Tungsuchat-Huang et al. 2011). Because the bar$^{au}$ gene is not suitable for the recovery of transplastomic clones in tissue culture (Lutz et al. 2001, Ye et al. 2003), the bar$^{au}$ gene currently is a component of a two-gene visual marker system, in which bar$^{au}$ is introduced into plastids by selection for a linked aadA gene. In applications for in planta plastid transformation bar$^{au}$ or aadA$^{au}$ alone is sufficient as a visual marker. Thus, the plastid transformation vector intended for in planta applications will have bar$^{au}$ or aadA$^{au}$ as a visual marker and one or more gene of interest, flanked by ptDNA fragments to target the insertion of the transgenes into the plastid genome. The transformation vector will be delivered to cells that are suitably positioned in the plant body to form a shoot apex. When the shoot apex derives from DNA-treated cells sprouts, the transplastomic clones will be recognized as aurea leaf sectors. Collection of transplastomic seed will be guided by the position of aurea sectors in the plants, as described above.

As for the method of DNA delivery, the biolistic protocol could be directly applied to an axillary bud site (Finer et al. 1992, Sanford et al. 1993, Ye et al. 1990). This could be accomplished with hand-held versions of the biolistic gun, such as the Helios Gene Gun. In one approach, the bud could be excised, and cells in the proper anatomical position bombarded in a PDS-1000He biolistic device. The bud so treated is then grafted onto a proper rootstock to grow shoots from the bombarded tissue. Alternatively, to provide a suitable vacuum, the current version of the biolistic gun could be modified to partially enclose the plant's body in a vacuum chamber. An alternative method for DNA delivery would be re-engineering the *Agrobacterium's* molecular machinery to target the T-DNA to plastids. If successful, Agroinjection could be applied for in plantaplastid transformation as it is done today for in planta excision of plastid marker genes.

References for Examples II and III

Cardi, T., Lenzi, P. and Maliga, P. (2010) Chloroplasts as expression platforms for plant-produced vaccines. *Expert Rev Vaccines*, 9, 893-911.

Carrer, H., Staub, J. M. and Maliga, P. (1990) Gentamycin resistance in *Nicotiana* conferred by AAC(3)-I, a narrow substrate specificity acetyl transferase. *Plant Mol Biol*, 17, 301-303.

Clough, S. J. and Bent, A. F. (1998) Floral dip: a simplified method for *Agrobacterium*-mediated transformation of *Arabidopsis thaliana*. *Plant J*, 16, 735-743.

Corneille, S., Lutz, K., Svab, Z. and Maliga, P. (2001) Efficient elimination of selectable marker genes from the plastid genome by the CRE-lox site-specific recombination system. *Plant J,* 72, 171-178.

Corneille, S., Lutz, K. A., Azhagiri, A. K. and Maliga, P. (2003) Identification of functional lox sites in the plastid genome. *Plant J,* 35, 753-762.

Davarpanah, S. J., Jung, S. H., Kim, Y. J., Park, Y. I., Min, S. R., Liu, J. R. and Jeong, W. J. (2009) Stable Plastid Transformation in Nicotiana benthamiana. *J Plant Biol,* 52, 244-250.

Day, A. and Goldschmidt-Clermont, M. (2011) The chloroplast transformation toolbox: selectable markers and marker removal. *Plant Biotechnol J,* 9, 540-553.

Desfeux, C., Clough, S. J. and Bent, A. F. (2000) Female reproductive tissues are the primary target of *Agrobacterium*-mediated transformation by the *Arabidopsis* floral-dip method. *Plant Physiol,* 123, 895-904.

Dufourmantel, N., Pelissier, B., Garcon, F., Peltier, G., Ferullo, J. M. and Tissot, G. (2004) Generation of fertile transplastomic soybean. *Plant Mol Biol,* 55, 479-489.

Finer, J. J., Vain, P., Jones, M. W. and McMullen, M. D. (1992) Development of the particle inflow gun for DNA delivery to plant cells. *Plant Cell Rep,* 11, 323-328.

Hajdukiewicz, P. T. J., Gilbertson, L. and Staub, J. M. (2001) Multiple pathways for Cre/lox-mediated recombination in plastids. *Plant J,* 27, 161-170.

Kanamoto, H., Yamashita, A., Asao, H., Okumura, S., Takase, H., Hattori, M., Yokota, A. and Tomizawa, K. (2006) Efficient and stable transformation of *Lactuca sativa* L. cv. Cisco (lettuce) plastids. *Transgenic Res,* 15, 205-217.

Kittiwongwattana, C., Lutz, K. A., Clark, M. and Maliga, P. (2007) Plastid marker gene excision by the phiC31 phage site-specific recombinase. *Plant Mol Biol,* 64, 137-143.

Liu, C. W., Lin, C. C., Chen, J. J. and Tseng, M. J. (2007) Stable chloroplast transformation in cabbage (*Brassica oleracea* L. var. *capitata* L.) by particle bombardment. *Plant Cell Rep,* 26, 1733-1744.

Lutz, K., Corneille, S., Azhagiri, A. K., Svab, Z. and Maliga, P. (2004) A novel approach to plastid transformation utilizes the phiC31 phage integrase. *Plant J,* 37, 906-913.

Lutz, K. A., Bosacchi, M. H. and Maliga, P. (2006a) Plastid marker gene excision by transiently expressed CRE recombinase. *Plant J,* 45, 447-456.

Lutz, K. A., Knapp, J. E. and Maliga, P. (2001) Expression of bar in the plastid genome confers herbicide resistance. *Plant Physiol,* 125, 1585-1590.

Lutz, K. A. and Maliga, P. (2007) Construction of marker-free transplastomic plants. *Curr Opin Biotechnol,* 18, 107-114.

Lutz, K. A. and Maliga, P. (2008) Plastid genomes in a regenerating tobacco shoot derive from a small number of copies selected through a stochastic process. *Plant J,* 56, 975-983.

Lutz, K. A., Svab, Z. and Maliga, P. (2006b) Construction of marker-free transplastomic tobacco using the Cre-loxP site-specific recombination system. *Nat Protocols,* 1, 900-910.

Maliga, P. (2004) Plastid transformation in higher plants. *Ann Rev Plant Biol,* 55, 289-313.

Maliga, P. and Bock, R. (2011) Plastid biotechnology: food, fuel and medicine for the 21st century. *Plant Physiol,* 155, 1501-1510.

Maliga, P. and Svab, Z. (2011) Engineering the plastid genome of *Nicotiana sylvestris*, a diploid model species for plastid genetics In *Plant chromosome engineering: methods and protocols* (Birchler, J. J. ed. New York: Springer Science+Business Media, LLC, pp. 37-50.

Murray, M. G., Palmer, J. D., Cuellar, R. E. and Thompson, W. F. (1979) Deoxyribonucleic acid sequence organization in the mung bean genome. *Biochemistry,* 18, 5259-5266.

O'Neill, C., Horvath, G. V., Horvath, E., Dix, P. J. and Medgyesy, P. (1993) Chloroplast transformation in plants: polyethylene glycol (PEG) treatment of protoplasts is an alternative to biolistic delivery systems. *Plant J,* 3, 729-738.

Poethig, S. (1989) Genetic mosaics and cell lineage analysis in plants. *Trends in Genetics,* 5, 273-277.

Raubeson, L. A. and Jansen, R. K. (2005) Chloroplast genomes of plants. In *Diversity and Evolution of Plants—Genotypic and Phenotypic Variation in Higher Plants* (Henry, R. J. ed. Wallingford, UK: CABI Publishing, pp. 45-68.

Ruf, S., Hermann, M., Berger, I. J., Carrer, H. and Bock, R. (2001) Stable genetic transformation of tomato plastids: foreign protein expression in fruit. *Nat Biotechnol,* 19, 870-875.

Ruhlman, T., Verma, D., Samson, N. and Daniell, H. (2010) The role of heterologous chloroplast sequence elements in transgene integration and expression. *Plant Physiol,* 152, 2088-2104.

Sanford, J. C., Smith, F. D. and Russell, J. A. (1993) Optimizing the biolistic process for different biological applications. *Methods Enzymol,* 217, 483-509.

Singh, A. K., Verma, S. S. and Bansal, K. C. (2010) Plastid transformation in eggplant (*Solanum melongena* L.). *Transgenic Res,* 19, 113-119.

Svab, Z. and Maliga, P. (1993) High-frequency plastid transformation in tobacco by selection for a chimeric aadA gene. *Proc Natl Acad Sci USA,* 90, 913-917.

Tungsuchat-Huang, T., Sinagawa-Garcia, S. R., Paredes-Lopez, O. and Maliga, P. (2010) Study of plastid genome stability in tobacco reveals that the loss of marker genes is more likely by gene conversion than by recombination between 34-bp loxP repeats. *Plant Physiol,* 153, 252-259.

Tungsuchat-Huang, T., Slivinski, K. M., Sinagawa-Garcia, S. R. and Maliga, P. (2011) Visual spectinomycin resistance gene for facile identification of transplastomic sectors in tobacco leaves. *Plant Mol Biol,* 76, 453-461.

Valkov, V. T., Gargano, D., Manna, C., Formisano, G., Dix, P. J., Gray, J. C., Scotti, N. and Cardi, T. (2011) High efficiency plastid transformation in potato and regulation of transgene expression in leaves and tubers by alternative 5' and 3' regulatory sequences. *Transgenic Res,* 20, 137-151.

Wei, Z., Liu, Y., Lin, C., Wang, Y., Cai, Q., Dong, Y. and Xing, S. (2011) Transformation of alfalfa chloroplasts and expression of green fluorescent protein in a forage crop. *Biotechnology letters,* 33, 2487-2494.

Ye, G. N., Colburn, S., Xu, C. W., Hajdukiewicz, P. T. J. and Staub, J. M. (2003) Persistence of unselected transgenic DNA during a plastid transformation and segregation approach to herbicide resistance. *Plant Physiol,* 133, 402-410.

Ye, G. N., Daniell, H. and Sanford, J. C. (1990) Optimization of delivery of foreign DNA into higher-plant chloroplasts. *Plant Mol Biol,* 15, 809-819.

Zubko, M. K., Zubko, E. I., van Zuilen, K., Mayer, P. and Day, A. (2004) Stable transformation of petunia plastids. *Transgenic Res,* 13, 523-530. While the invention has been described in detail and with reference to specific examples thereof, it will be apparent to one skilled in the art that various changes and modifications can be made therein without departing from the spirit and scope thereof.

What is claimed is:

1. An isolated nucleic acid encoding a visibly detectable selectable marker for identification of transformed plastids, wherein said nucleic acid encodes aadA$^{au}$ protein of SEQ ID NO: 7 and confers the aurea phenotype under culture and greenhouse conditions.

2. A plant transformation vector comprising the isolated nucleic acid of claim 1 suitable to transform plastids of higher plants.

3. The vector of claim 2, comprising a multiple-cloning site suitable for insertion of a heterologous nucleic acid encoding a protein of interest.

4. The vector of claim 3, which is pKMS8 (SEQ ID NO: 6).

5. The vector of claim 3, comprising a heterologous nucleic acid encoding a molecule selected from the group consisting of a drought resistance protein, an herbicide resistance protein, a cytokine, an siRNA, a miRNA, shRNA, an antisense RNA, an antibody, a hormone, a receptor and a ligand.

6. A plant cell transformed with the vector of claim 3.

7. A plant comprising the cell of claim 6.

8. A method for obtaining transplastomic plants, said method comprising introducing the nucleic acid of claim 1 into a plant cell, selecting those transformed cells which exhibit a golden leaf phenotype and spectinomycin resistance under culture and green house conditions, regenerating shoots from said transformed cells, and rooting said shoots in soil under conditions suitable to generate said transplastomic plant.

9. A method for obtaining transplastomic plants, said method comprising introducing the vector of claim 3 into a plant cell, selecting those transformed cells which exhibit a golden leaf phenotype and spectinomycin resistance under culture and greenhouse conditions, regenerating shoots from said transformed cells, and rooting said shoots in soil under conditions suitable to generate said transplastomic plant.

10. A transplastomic plant obtained by the method of claim 9.

11. The plant of claim 10 which is a monocot or a dicot.

* * * * *

SEQUENCE LISTING

<160> NUMBER OF SEQ ID NOS: 7

<210> SEQ ID NO 1
<211> LENGTH: 144
<212> TYPE: DNA
<213> ORGANISM: Artificial Sequence
<220> FEATURE:
<223> OTHER INFORMATION: PrrnPclpPrbcL

<400> SEQUENCE: 1
gagctcgctc cccgccgtc gttcaatgag aatggataag aggctcgtgg gattgacgtg      60 aggggcagg gatggctata tttctgggag ttacgtttcc acctcaaagt gaaatatagt     120
atagttgtag ggagggatcc atgg                                           144

<210> SEQ ID NO 2
<211> LENGTH: 196
<212> TYPE: DNA
<213> ORGANISM: Artificial Sequence
<220> FEATURE:
<223> OTHER INFORMATION: PrrnPclpP+DB

<400> SEQUENCE: 2
gagctcgctc cccgccgtc gttcaatgag aatggataag aggctcgtgg gattgacgtg      60 aggggcagg gatggctata tttctgggag ttacgtttcc acctcaaagt gaaatatagt     120
atttagttct ttctttcatt taatgcctat tggtgttcca aaagtcccctt tccgaagtcc   180 tggagaggaa gctagc                                                    196

<210> SEQ ID NO 3
<211> LENGTH: 154
<212> TYPE: DNA
<213> ORGANISM: Artificial Sequence
<220> FEATURE:
<223> OTHER INFORMATION: PrrnPclp

<400> SEQUENCE: 3
gagctcgctc cccgccgtc gttcaatgag aatggataag aggctcgtgg gattgacgtg      60 aggggcagg gatggctata tttctgggag ttacgtttcc acctcaaagt gaaatatagt     120
atttagttct ttctttcatt taatgcctgc tagc                                154

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ggcttcaggc cgccatccac t                                               21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gtagttaatg gtagggttac c                                               21

<210> SEQ ID NO 6
<211> LENGTH: 7407

<212> TYPE: DNA
<213> ORGANISM: Artificial Sequence
<220> FEATURE:
<223> OTHER INFORMATION: aurea aadAau

<400> SEQUENCE: 6

```
aattcaccgc cgtatggctg accggcgatt actagcgatt ccggcttcat gcaggcgagt      60
tgcagcctgc aatccgaact gaggacgggt ttttggggtt agctcaccct cgcgggatcg     120
cgacccttg tcccggccat tgtagcacgt gtgtcgccca gggcataagg ggcatgatga      180
cttgacgtca tcctcacctt cctccggctt atcaccggca gtctgttcag ggttccaaac     240
tcaacgatgg caactaaaca cgagggttgc gctcgttgcg ggacttaacc caacaccttta    300
cggcacgagc tgacgacagc catgcaccac ctgtgtccgc gttcccgaag gcacccctct     360
ctttcaagag gattcgcggc atgtcaagcc ctggtaaggt tcttcgcttt gcatcgaatt     420
aaaccacatg ctccaccgct tgtgcgggcc cccgtcaatt cctttgagtt tcattcttgc     480
gaacgtactc cccaggcggg atacttaacg cgttagctac agcactgcac gggtcgatac     540
gcacagcgcc tagtatccat cgtttacggc taggactact ggggtatcta atcccattcg     600
ctccctagc tttcgtctct cagtgtcagt gtcggcccag cagagtgctt cgccgttgg      660
tgttctttcc gatctctacg catttcaccg ctccaccgga aattccctct gccctaccg     720
tactccagct tggtagtttc caccgcctgt ccagggttga gccctgggat ttgacgcgg     780
acttaaaaag ccacctacag acgctttacg cccaatcatt ccggataacg cttgcatcct    840
ctgtattacc gcggctgctg gcacagagtt agccgatgct tattcccag ataccgtcat     900
tgcttcttct ccgggaaaag aagttcacga cccgtgggcc ttctacctcc acgcggcatt    960
gctccgtcag gctttcgccc attgcggaaa attccccact gctgcctccc gtaggagtct    1020
gggccgtgtc tcagtcccag tgtggctgat catcctctcg gaccagctac tgatcatcgc    1080
cttggtaagc tattgcctca ccaactagct aatcagacgc gagcccctcc tcgggcggat    1140
tcctcctttt gctcctcagc ctacggggta ttagcagccg tttccagctg ttgttcccct    1200
cccaagggca ggttcttacg cgttactcac ccgtccgcca ctggaaacac cacttcccgt    1260
ccgacttgca tgtgttaagc atgccgccag cgttcatcct gagccaggat cgaactctcc    1320
atgagattca tagttgcatt acttatagct tccttgttcg tagacaaagc ggattcggaa    1380
ttgtcttca ttccaaggca taacttgtat ccatgcgctt catattcgcc cggagttcgc     1440
tcccagaaat atagccatcc ctgcccctc acgtcaatcc cacgagcctc ttatccattc     1500
tcattgaacg acggcgggg agctttcgag gcctcgaaat ccaactagaa aaactcacat     1560
tgggcttagg gataatcagg ctcgaactga tgacttccac cacgtcaagg tgacactcta    1620
ccgctgagtt atatcccttc cccgcccat cgagaaatag aactgactaa tcctaagtca     1680
aagggtcgag aaactcaacg ccactattct tgaacaactt ggagccgggc cttcttttcg    1740
cactattacg gatatgaaaa taatggtcaa aatcggattc aattgtcaaa gtactcacag    1800
tttaaactgt ggaattcgag ctcggtaccc ggggatcctc tagagtcgac ctgcaggcat    1860
gcaagcttga tgatttcgct ccccgccgt cgttcaatga aatggataa gaggctcgtg      1920
ggattgacgt gaggggcag ggatggctat atttctggga gttacgtttc cacctcaaag    1980
tgaaatatag tatttagttc tttctttcat ttaatgccta ttggtgttcc aaaagtccct    2040
ttccgaagtc ctggagagga agctactagc gaagcggtga tcgccgaagt atcgactcaa    2100
ctatcagagg tagttggcgt catcgagcgc catctcgaac cgacgttgct ggccgtacat    2160
```

```
ttgtacggct ccgcagtgga tggcggcctg aagccacaca gtgatattga tttgctggtt   2220
acggtgaccg taaggcttga tgaaacaacg cggcgagctt tgatcaacga ccttttggaa   2280
acttcggctt cccctggaga gagcgagatt ctccgcgctg tagaagtcac cattgttgtg   2340
cacgacgaca tcattccgtg gcgttatcca gctaagcgcg aactgcaatt tggagaatgg   2400
cagcgcaatg acattcttgc aggtatcttc gagccagcca cgatcgacat tgatctggct   2460
atcttgctga caaaagcaag agaacatagc gttgccttgg taggtccagc ggcggaggaa   2520
ctctttgatc cggttcctga acaggatcta tttgaggcgc taaatgaaac cttaacgcta   2580
tggaactcgc cgcccgactg ggctggcgat gagcgaaatg tagtgcttac gttgtcccgc   2640
atttggtaca gcgcagtaac cggcaaaatc gcgccgaagg atgtcgctgc cgactgggca   2700
atggagcgcc tgccggccca gtatcagccc gtcatacttg aagctagaca ggcttatctt   2760
ggacaagaag aagatcgctt ggcctcgcgc gcagatcagt tggaagaatt tgtccactac   2820
gtgaaaggcg agatcaccaa ggtagtgggc aaagaacaaa aactcatttc tgaagaagac   2880
ttgtgagtct agctagagcg atcctggcct agtctatagg aggttttgaa agaaaggag    2940 caataatcat tttcttgttc tatcaagagg gtgctattgc tcctttcttt ttttcttttt   3000
atttatttac tagtatttta cttacataga ctttttttgtt tacattatag aaaaagaagg   3060
agaggttatt ttcttgcatt tattcatgaa gctaaatcat cgggcccagt actttaactg   3120
cccctatcgg aaataggatt gactaccgat tccgaaggaa ctggagttac atctcttttc   3180
cattcaagag ttcttatgcg tttccacgcc cctttgagac cccgaaaaat ggacaaattc   3240
cttttcttag gaacacatac aagattcgtc actacaaaaa ggataatggt aaccctacca   3300
ttaactactt catttatgaa tttcatagta atagaaatac atgtcctacc gagacagaat   3360
ttggaacttg ctatcctctt gcctagcagg caaagattta cctccgtgga aaggatgatt   3420
cattcggatc gacatgagag tccaactaca ttgccagaat ccatgttgta tatttgaaag   3480
aggttgacct ccttgcttct ctcatggtac actcctcttc ccgccgagcc ccttttctcc   3540
tcggtccaca gagacaaaat gtaggactgg tgccaacaat tcatcagact cactaagtcg   3600
ggatcactaa ctaatactaa tctaatataa tagtctaata tatctaatat aatagaaaat   3660
actaatataa tagaaaagaa ctgtctttttc tgtatacttt ccccggttcc gttgctaccg   3720
cgggctttac gcaatcgatc ggattagata gatatcccctt caacataggt catcgaaagg   3780
atctcggaga cccaccaaag tacgaaagcc aggatctttc agaaacgga ttcctattca    3840 aagagtgcat aaccgcatgg ataagctcac actaacccgt caatttggga tccaaattcg   3900
agattttcct tgggaggtat cgggaaggat ttggaatgga ataatatcga ttcatacaga   3960
agaaaaggtt ctctattgat tcaaacactg tacctaacct atgggatagg gatcgaggaa   4020
ggggaaaaac cgaagatttc acatggtact tttatcaatc tgatttattt cgtacctttc   4080
gttcaatgag aaaatgggtc aaattctaca ggatcaaacc tatgggactt aaggaatgat   4140
ataaaaaaaa gagagggaaa atattcatat taaataaata tgaagtagaa gaacccagat   4200
tccaaatgaa caaattcaaa cttgaaaagg atcttcctta ttcttgaaga atgagggggca   4260 aagggattga tcaagaaaga tcctctagct agagcttggc gtaatcatgg tcatagctgt   4320
ttcctgtgtg aaattgttat ccgctcacaa ttccacacaa catacgagcc ggaagcataa   4380
agtgtaaagc ctggggtgcc taatgagtga gctaactcac attaattgcg ttgcgctcac   4440
tgcccgcttt ccagtcggga aacctgtcgt gccagctgca ttaatgaatc ggccaacgcg   4500
cggggagagg cggtttgcgt attgggcgct cttccgcttc ctcgctcact gactcgctgc   4560
```

```
gctcggtcgt tcggctgcgg cgagcggtat cagctcactc aaaggcggta atacggttat    4620
ccacagaatc aggggataac gcaggaaaga acatgtgagc aaaaggccag caaaaggcca    4680
ggaaccgtaa aaaggccgcg ttgctggcgt ttttccatag gctccgcccc cctgacgagc    4740
atcacaaaaa tcgacgctca agtcagaggt ggcgaaaccc gacaggacta taaagatacc    4800
aggcgtttcc ccctggaagc tccctcgtgc gctctcctgt tccgaccctg ccgcttaccg    4860
gatacctgtc cgcctttctc ccttcgggaa gcgtggcgct ttctcatagc tcacgctgta    4920
ggtatctcag ttcggtgtag gtcgttcgct ccaagctggg ctgtgtgcac gaaccccccg    4980
ttcagcccga ccgctgcgcc ttatccggta actatcgtct tgagtccaac ccggtaagac    5040
acgacttatc gccactggca gcagccactg gtaacaggat tagcagagcg aggtatgtag    5100
gcggtgctac agagttcttg aagtggtggc ctaactacgg ctacactaga aggacagtat    5160
ttggtatctg cgctctgctg aagccagtta ccttcggaaa aagagttggt agctcttgat    5220
ccggcaaaca aaccaccgct ggtagcggtg gtttttttgt ttgcaagcag cagattacgc    5280
gcagaaaaaa aggatctcaa gaagatcctt tgatctttc tacgggtct gacgctcagt    5340 ggaacgaaaa ctcacgttaa gggattttgg tcatgagatt atcaaaaagg atcttcacct    5400
agatcctttt aaattaaaaa tgaagtttta atcaatcta agtatatat gagtaaactt    5460 ggtctgacag ttaccaatgc ttaatcagtg aggcacctat ctcagcgatc tgtctatttc    5520
gttcatccat agttgcctga ctccccgtcg tgtagataac tacgatacgg gagggcttac    5580
catctggccc cagtgctgca atgataccgc gagacccacg ctcaccggct ccagatttat    5640
cagcaataaa ccagccagcc ggaagggccg agcgcagaag tggtcctgca actttatccg    5700
cctccatcca gtctattaat tgttgccggg aagctagagt aagtagttcg ccagttaata    5760
gtttgcgcaa cgttgttgcc attgctacag gcatcgtggt gtcacgctcg tcgtttggta    5820
tggcttcatt cagctccggt tcccaacgat caaggcgagt tacatgatcc cccatgttgt    5880
gcaaaaaagc ggttagctcc ttcggtcctc cgatcgttgt cagaagtaag ttggccgcag    5940
tgttatcact catggttatg gcagcactgc ataattctct tactgtcatg ccatccgtaa    6000
gatgcttttc tgtgactggt gaatactcaa ccaagtcatt ctgagaatag tgtatgcggc    6060
gaccgagttg ctcttgcccg gcgtcaatac gggataatac cgcgccacat agcagaactt    6120
taaaagtgct catcattgga aaacgttctt cggggcgaaa actctcaagg atcttaccgc    6180
tgttgagatc cagttcgatg taacccactc gtgcacccaa ctgatcttca gcatctttta    6240
ctttcaccag cgtttctggg tgagcaaaaa caggaaggca aaatgccgca aaaagggaa    6300 taagggcgac acggaaatgt tgaatactca tactcttcct ttttcaatat tattgaagca    6360
tttatcaggg ttattgtctc atgagcggat acatatttga atgtatttag aaaaataaac    6420
aaataggggt tccgcgcaca tttccccgaa aagtgccacc tgacgtctaa gaaaccatta    6480
ttatcatgac attaacctat aaaaataggc gtatcacgag gccctttcgt ctcgcgcgtt    6540
tcggtgatga cggtgaaaac ctctgacaca tgcagctccc ggagacggtc acagcttgtc    6600
tgtaagcgga tgccgggagc agacaagccc gtcagggcgc gtcagcgggt gttggcgggt    6660
gtcggggctg gcttaactat gcggcatcag agcagattgt actgagagtg caccataaaa    6720
ttgtaaacgt taatattttg ttaaaattcg cgttaaattt ttgttaaatc agctcatttt    6780
ttaaccaata ggccgaaatc ggcaaaatcc cttataaatc aaaagaatag cccgagatag    6840
ggttgagtgt tgttccagtt tggaacaaga gtccactatt aaagaacgtg gactccaacg    6900
```

-continued

```
tcaaagggcg aaaaaccgtc tatcagggcg atggcccact acgtgaacca tcacccaaat    6960 caagttttt  ggggtcgagg tgccgtaaag cactaaatcg aaccctaaa  gggagccccc    7020 gatttagagc ttgacgggga aagccggcga acgtggcgag aaaggaaggg aagaaagcga    7080
aaggagcggg cgctagggcg ctggcaagtg tagcggtcac gctgcgcgta accaccacac    7140
ccgccgcgct taatgcgccg ctacagggcg cgtactatgg ttgctttgac gtatgcggtg    7200
tgaaataccg cacagatgcg taaggagaaa ataccgcatc aggcgccatt cgccattcag    7260
gctgcgcaac tgttgggaag ggcgatcggt gcgggcctct tcgctattac gccagctggc    7320
gaaaggggga tgtgctgcaa ggcgattaag ttgggtaacg ccagggtttt cccagtcacg    7380
acgttgtaaa acgacggcca gtgaatt                                        7407
```

<210> SEQ ID NO 7
<211> LENGTH: 290
<212> TYPE: PRT
<213> ORGANISM: Artificial Sequence
<220> FEATURE:
<223> OTHER INFORMATION: ClpP+aadAau

<400> SEQUENCE: 7

```
Met Pro Ile Gly Val Pro Lys Val Pro Phe Arg Ser Pro Gly Glu Glu
 1               5                  10                  15

Ala Thr Ser Glu Ala Val Ile Ala Glu Val Ser Thr Gln Leu Ser Glu
            20                  25                  30

Val Val Gly Val Ile Glu Arg His Leu Glu Pro Thr Leu Leu Ala Val
        35                  40                  45

His Leu Tyr Gly Ser Ala Val Asp Gly Gly Leu Lys Pro His Ser Asp
    50                  55                  60

Ile Asp Leu Leu Val Thr Val Thr Val Arg Leu Asp Glu Thr Thr Arg
65                  70                  75                  80

Arg Ala Leu Ile Asn Asp Leu Leu Glu Thr Ser Ala Ser Pro Gly Glu
                85                  90                  95

Ser Glu Ile Leu Arg Ala Val Glu Val Thr Ile Val Val His Asp Asp
            100                 105                 110

Ile Ile Pro Trp Arg Tyr Pro Ala Lys Arg Glu Leu Gln Phe Gly Glu
        115                 120                 125

Trp Gln Arg Asn Asp Ile Leu Ala Gly Ile Phe Glu Pro Ala Thr Ile
    130                 135                 140

Asp Ile Asp Leu Ala Ile Leu Leu Thr Lys Ala Arg Glu His Ser Val
145                 150                 155                 160

Ala Leu Val Gly Pro Ala Ala Glu Glu Leu Phe Asp Pro Val Pro Glu
                165                 170                 175

Gln Asp Leu Phe Glu Ala Leu Asn Glu Thr Leu Thr Leu Trp Asn Ser
            180                 185                 190

Pro Pro Asp Trp Ala Gly Asp Glu Arg Asn Val Val Leu Thr Leu Ser
        195                 200                 205

Arg Ile Trp Tyr Ser Ala Val Thr Gly Lys Ile Ala Pro Lys Asp Val
    210                 215                 220

Ala Ala Asp Trp Ala Met Glu Arg Leu Pro Ala Gln Tyr Gln Pro Val
225                 230                 235                 240

Ile Leu Glu Ala Arg Gln Ala Tyr Leu Gly Gln Glu Asp Arg Leu
                245                 250                 255

Ala Ser Arg Ala Asp Gln Leu Glu Glu Phe Val His Tyr Val Lys Gly
            260                 265                 270
```

-continued

```
Glu Ile Thr Lys Val Val Gly Lys Glu Gln Lys Leu Ile Ser Glu Glu
        275                 280                 285

Asp Leu
    290
```